(12) United States Patent
Andresen

(10) Patent No.: US 11,547,760 B2
(45) Date of Patent: Jan. 10, 2023

(54) REVERSIBLE LINKERS AND USE THEREOF

(71) Applicant: Torque Therapeutics, Inc., Cambridge, MA (US)

(72) Inventor: Thomas L. Andresen, Cambridge, MA (US)

(73) Assignee: Torque Therapeutics, Inc., Cambridge, MA (US)

( * ) Notice: Subject to any disclaimer, the term of this patent is extended or adjusted under 35 U.S.C. 154(b) by 133 days.

(21) Appl. No.: 16/644,675

(22) PCT Filed: Sep. 5, 2018

(86) PCT No.: PCT/US2018/049594
§ 371 (c)(1),
(2) Date: Mar. 5, 2020

(87) PCT Pub. No.: WO2019/050977
PCT Pub. Date: Mar. 14, 2019

(65) Prior Publication Data
US 2021/0154313 A1 May 27, 2021

Related U.S. Application Data

(60) Provisional application No. 62/554,067, filed on Sep. 5, 2017, provisional application No. 62/616,221, filed on Jan. 11, 2018.

(51) Int. Cl.
| | | |
|---|---|---|
| *A61K 47/65* | (2017.01) | |
| *C07D 403/12* | (2006.01) | |
| *A61K 47/69* | (2017.01) | |
| *A61K 47/64* | (2017.01) | |
| *C07D 207/46* | (2006.01) | |
| *C07K 14/54* | (2006.01) | |

(52) U.S. Cl.
CPC ............ *A61K 47/65* (2017.08); *A61K 47/645* (2017.08); *A61K 47/6903* (2017.08); *A61K 47/6935* (2017.08); *C07D 207/46* (2013.01); *C07D 403/12* (2013.01); *C07K 14/5443* (2013.01)

(58) Field of Classification Search
None
See application file for complete search history.

(56) References Cited

U.S. PATENT DOCUMENTS

| | | | |
|---|---|---|---|
| 4,085,269 A | 4/1978 | Daumiller et al. | |
| 4,549,010 A | 10/1985 | Sparer et al. | |
| 6,521,431 B1 | 2/2003 | Kiser et al. | |
| 6,613,582 B1 | 9/2003 | Kodadek et al. | |
| 6,627,460 B1 | 9/2003 | Lihme et al. | |
| 6,887,974 B2 | 5/2005 | Pathak | |
| 7,011,812 B1 | 3/2006 | Griffiths et al. | |
| 7,531,572 B2 | 5/2009 | Dai et al. | |
| 7,604,804 B2 | 10/2009 | Wang et al. | |
| 7,648,962 B2 | 1/2010 | James et al. | |
| 7,662,773 B2 | 2/2010 | James et al. | |
| 8,349,901 B2 | 1/2013 | Satyam | |
| 8,440,309 B2 | 5/2013 | Ohri et al. | |
| 8,562,965 B2 | 10/2013 | McManus et al. | |
| 8,580,545 B2 | 11/2013 | Alferiev et al. | |
| 9,504,643 B2 | 11/2016 | Tice et al. | |
| 9,603,944 B2 | 3/2017 | Tang et al. | |
| 2003/0078339 A1 | 4/2003 | Kiser et al. | |
| 2006/0074009 A1 | 4/2006 | James et al. | |
| 2006/0100163 A1 | 5/2006 | Orlando et al. | |
| 2008/0207505 A1 | 8/2008 | James | |
| 2011/0262963 A1 | 10/2011 | Geierstanger et al. | |
| 2014/0081012 A1 | 3/2014 | DeSimone et al. | |
| 2014/0249319 A1* | 9/2014 | Nguyen ............ | C07D 207/452 548/518 |
| 2017/0065726 A1 | 3/2017 | Huang | |
| 2017/0080104 A1 | 3/2017 | Irvine et al. | |
| 2021/0060065 A1 | 3/2021 | Andresen | |

FOREIGN PATENT DOCUMENTS

| | | |
|---|---|---|
| EP | 3049114 A2 | 8/2016 |
| GB | 1112021 A | 5/1968 |
| WO | WO-2013012961 A2 | 1/2013 |
| WO | WO-2015048498 A3 | 7/2015 |
| WO | WO-2019050978 A1 | 3/2019 |

OTHER PUBLICATIONS

El-Giamal et al., "Über Einige Copolyurethane Ausgehend von Piperazin," Macromol. Chem. Phys. 177:2259-2269 (1976).
Festel et al., "Synthesis and Properties of Segmented Polyurethane Elastomers with Molecularly Uniform Hard Segments Based on 1,5-Naphthalene Diisocyanate and 1,4-Butandiol," Gaofenzi Tongbao 6:42-62 (2004).
Nuhn et al., "pH-Degradable Imidazoquinoline-Ligated Nanogels for Lymph Node-Focused Immune Activation," PNAS 113(29):8098-8103 (2016).
Written Opinion of the International Search Authority in International Application No. PCT/US2018/049594 dated Oct. 29, 2018.
Wu et al., "Synthesis and Performance of Hot Melt Polyurethane Adhesives based on Diels-Alder Reaction," Gaofenzi Cailiao Kexue Yu Gongcheng 31:1-5 (2015).
Zahn et al., "Isolierung und Synthese von Oligomeren aus Hexamethylen-di-isocyanat und Butandiol-(1.4),"Chem. Ber. 94:125-131 (1961).
Zahn et al., "Lineare Oligomere aus Hexamethylendiisocyanat und Butandiol-(1,4)," Macromol. Chem. Phys. 44:290-311 (1961).
International Search Report in International Application No. PCT/US2018/049594 dated Oct. 29, 2018.
International Preliminary Report on Patentability in International Application No. PCT/US2018/049594 dated May 9, 2019.
U.S. Appl. No. 16/644,647, Therapeutic Protein Compositions and Methods of Making and Using the Same, filed Mar. 5, 2020, Pending.

* cited by examiner

*Primary Examiner* — Thomas S Heard
(74) *Attorney, Agent, or Firm* — Goodwin Procter LLP

(57) ABSTRACT

Disclosed herein are compositions and methods for preparation and delivery of protein therapeutics, and more particularly reversible linkers and use thereof.

2 Claims, 29 Drawing Sheets

REVERSIBLE LINKERS AND USE THEREOF

CROSS REFERENCE TO RELATED APPLICATIONS

This application is a U.S. National Phase application under 35 U.S.C. 371 of International Application No. PCT/US2018/049594, filed Sep. 5, 2018, which claims priority to and the benefit of U.S. Provisional Application Nos. 62/554,067 filed Sep. 5, 2017 and 62/616,221 filed Jan. 11, 2018, the disclosures of each of which applications are hereby incorporated herein by reference in its entirety.

FIELD

The present disclosure generally relates to compositions and methods for preparation and delivery of protein therapeutics, and more particularly reversible linkers and use thereof.

BACKGROUND

Protein therapeutics, such as antibodies, cytokines, growth factors and vaccines, are important therapeutics for the treatment of a variety of diseases including, for example, cancer, diabetes and cardiovascular diseases. This class of protein therapeutics has been developed rapidly in the global pharmaceutical industry over the last few years. Protein therapeutics have the advantages of high specificity and potency relative to small molecule drugs. Nonetheless, the use of protein therapeutics is limited as a result of their intrinsic instability, immunogenicity and short half-life.

To address these limitations, there are generally two approaches: one is genetic fusion of the therapeutic protein, and the other is use of engineered carriers to deliver protein therapeutics. With engineered carriers, proteins are loaded by either encapsulation/adsorption or conjugation. Encapsulation or adsorption of proteins in/onto liposomes or nanoparticles is typically inefficient. Conjugation of proteins typically reduces their bioactivity. Therefore, both approaches are problematic.

Thus, a significant need exists for new compositions and methods that incorporate therapeutics into a delivery system with high efficiency.

SUMMARY

Disclosed herein are improved methods and compositions for improved linkers for therapeutic use.

In one aspect, disclosed herein is a compound having formula (I):

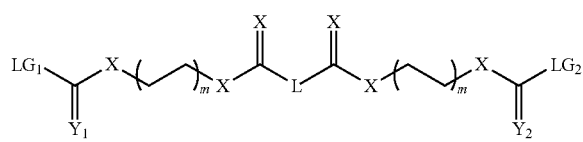

(I)

wherein:
LG$_1$ and LG$_2$ are each a leaving group, independently selected from triflate, tosyl, Cl, N-hydroxysuccinimide and imidazolide;
Y$_1$ and Y$_2$ are each independently selected from O and S;
X, at each occurrence, is independently selected from O, S, and N;
L is a linker such that

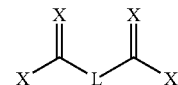

is biodegradable; and
m, at each occurrence, is an integer selected from 1-6.

In some embodiments, the compound of formula (I) is symmetrical.

In some embodiments, LG$_1$ and LG$_2$ are capable of reacting with a protein, a drug and/or a particle. In one example, LG$_1$ and LG$_2$ are both imidazolide. In another example, LG$_1$ and LG$_2$ are both N-hydroxysuccinimide.

In some embodiments,

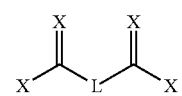

is hydrolysable.

In some embodiments, e.g., when one or more X is N, L is selected from:
(a) —(CH$_2$)$_n$— wherein n is an integer selected from 0-5;

(b)

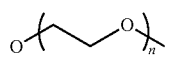

wherein n is an integer selected from 0-5; or (c)

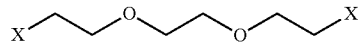

wherein X, at each occurrence, is independently selected from O, S, and N.

In some embodiments, m is 2.

A further aspect relates to a compound having formula (II):

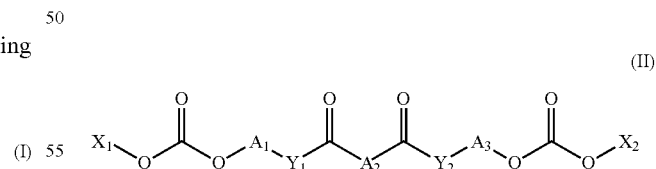

(II)

wherein:
X$_1$ and X$_2$ are each independently selected from triflate, tosyl, Cl, N-hydroxysuccinimide and imidazolide;
A$_1$ and A$_3$ are each independently —(CR$^1$R$^2$)$_n$—;
A$_2$ is —(CR$^1$R$^2$)$_m$—;
Y$_1$ and Y$_2$ are each independently selected from NR$^3$, O and S;
wherein R$^1$ and R$^2$ at each occurrence are independently selected from hydrogen, halogen, hydroxyl, C$_{1-12}$ alkyl, C$_{2-12}$ alkenyl, C$_{3-12}$ cycloalkyl, C$_{2-12}$ heterocyclyl; C$_{6-12}$ aryl optionally substituted with 1 or more halo, hydroxyl, $C_{1-6}$ alkyl and/or $C_{1-6}$ alkoxyl; and $C_{4-12}$ heteroaryl optionally substituted with 1 or more halo, hydroxyl, $C_{1-6}$ alkyl and/or $C_{1-6}$ alkoxyl wherein $R^3$ is selected from hydrogen, $C_{1-12}$ alkyl, $C_{2-12}$ alkenyl, $C_{3-12}$ cycloalkyl, $C_{2-12}$ heterocyclyl; $C_{6-12}$ aryl optionally substituted with 1 or more halo, hydroxyl, $C_{1-6}$ alkyl and/or $C_{1-6}$ alkoxyl; and $C_{4-12}$ heteroaryl optionally substituted with 1 or more halo, hydroxyl, $C_{1-6}$ alkyl and/or $C_{1-6}$ alkoxyl;

n, at each occurrence, is an integer independently selected from 1-12; and m is an integer selected from 0-12.

In some embodiments, the compound of formula (II) is symmetrical. In some embodiments, $X_1$ and $X_2$ can each be a leaving group capable of reacting with a protein, a drug and/or a particle. In one example, $X_1$ and $X_2$ are both imidazolide. In another example, $X_1$ and $X_2$ are both N-hydroxysuccinimide. In some embodiments, $R^1$ and $R^2$ are both hydrogen. In one example, $A_1$ and $A_3$ are both —$(CH_2)_2$—. In one embodiment, $A_2$ is —$(CH_2)_2$—. In some embodiments, $Y_1$ and $Y_2$ are both O.

In one embodiment, the compound is:

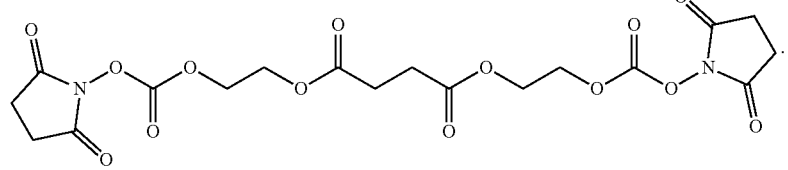

In some embodiments, $A_2$ is a bond. In one embodiment, $Y_1$ and $Y_2$ are both NH.

The compound, in some embodiments, is:

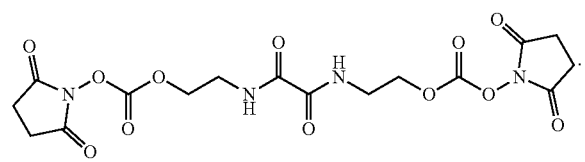

As disclosed herein, the compound may be used to conjugate or cross-link one or more protein or agent of interest at, e.g., an amine group such as a terminal amine or an internal amine. Internal amines include side chain amines such as lysine amines.

In certain embodiments, the compounds disclosed herein can be used to reversibly crossed-link a plurality of therapeutic protein monomers into protein clusters of, e.g., 30 nm and 1000 nm in diameter. The protein clusters can be subject to surface modification such as polycation. In some embodiments, these protein clusters are referred to as "backpacks" or "BP."

In various embodiments, a cell therapy composition can be prepared by providing the protein clusters or backpacks disclosed herein, and incubating the protein clusters or backpacks with a nucleated cell such as T cell, B cell, natural killer (NK) cell and hematopoietic stem cell. T cells can include CD4+T cells, cytotoxic T cells (e.g., CD8+ T cells), alpha T cells, beta T cells, gamma T cells, delta T cells and regulatory T-cell (Tregs). In some embodiments, the nucleated cell (e.g., T cell or NK cell) may comprise, e.g., express, a Chimeric Antigen Receptor (CAR) such as a CAR that binds to a cancer antigen.

In some embodiments, the compound can be used as a degradable or hydrolysable linker. In some embodiments, the degradable linker is a redox responsive linker. Methods of making and using various linkers (e.g., to make nanogels or backpacks) are disclosed in U.S. Publication No. 2017/0080104, U.S. Pat. No. 9,603,944, and U.S. Publication No. 2014/0081012, each of which is incorporated herein by reference in its entirety.

In another aspect, the disclosure provides a particle, e.g., a nanoparticle, that is formed by the linkers as described herein, e.g., nanoparticle that comprises a protein (e.g., a protein nanogel). Nanoparticles and methods of making are disclosed in PCT International Application No. PCT/US2017/037249 filed Jun. 13, 2017, e.g., on pages 57-79, which is incorporated herein by reference in its entirety. In certain embodiments, the linkers disclosed herein can be used in connection with the backpack technology for e.g., cell therapy as disclosed in, e.g., U.S. Publication No. 2017/0080104, U.S. Pat. No. 9,603,944, U.S. Publication No. 2014/0081012, and PCT Application No. PCT/US2017/037249, each of which is incorporated herein by reference in its entirety.

BRIEF DESCRIPTION OF THE DRAWINGS

As shown in FIG. 11, Linker-1 NG and Linker-2 NG both displayed anti-tumor activity.

DETAILED DESCRIPTION

Figure 1:
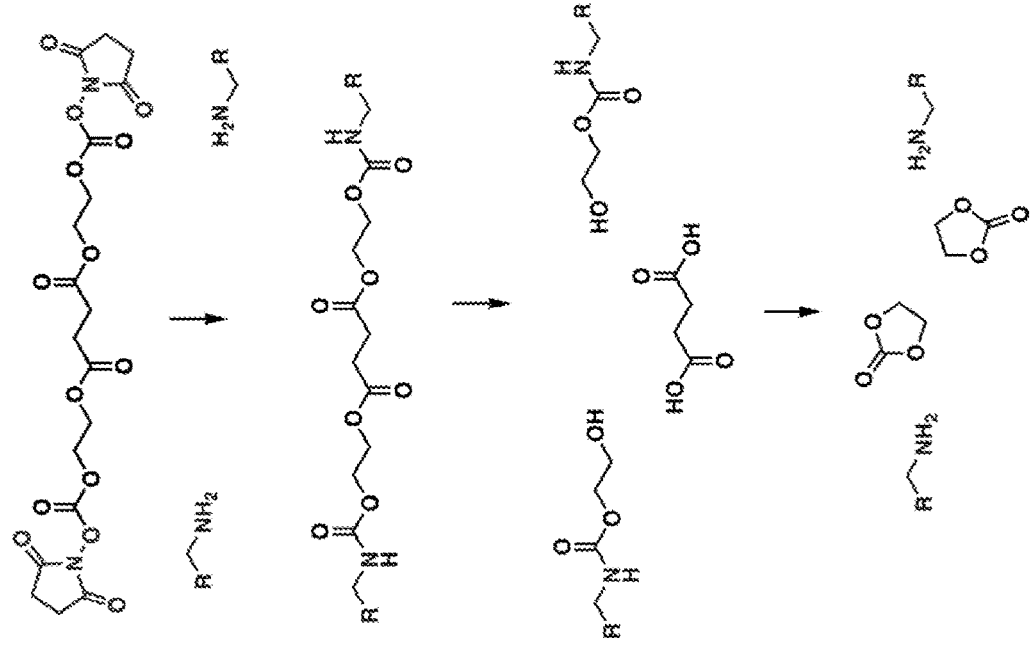
FIG. 1 illustrates two exemplary linkers, Linker-1 and Linker-2.
Figure 1:
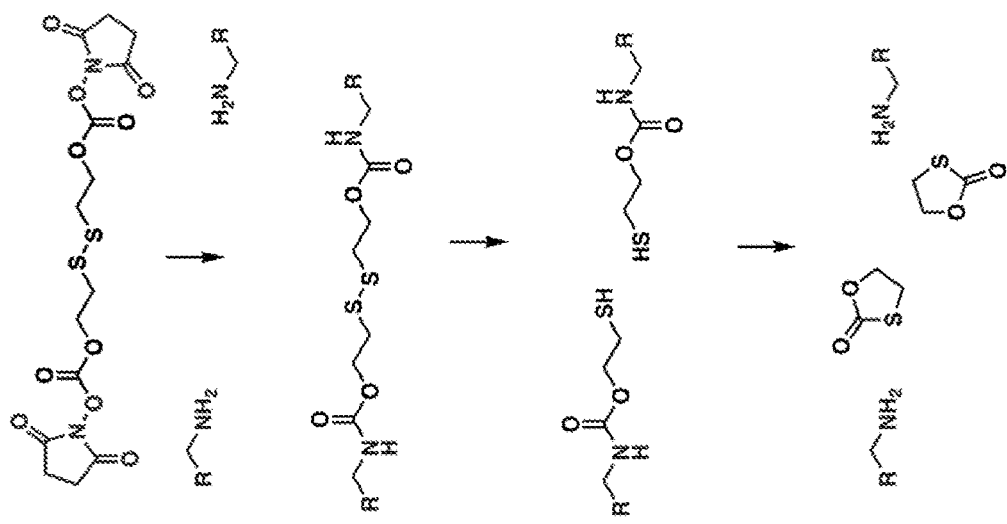

Cancer immunotherapy, including adoptive T cell therapy, is a promising strategy to treat cancer because it harnesses a subject's own immune system to attack cancer cells. Nonetheless, a major limitation of this approach is the rapid decline in viability and function of the transplanted T lymphocytes. In order to maintain high numbers of viable tumor-specific cytotoxic T lymphocytes in tumors, co-administration of immunostimulatory agents with transferred cells is necessary. When given systemically at high doses, these agents could enhance the in vivo viability of transferred (i.e., donor) cells, improve the therapeutic function of transferred cells, and thus lead to overall improved efficacy against cancer; however, high doses of such agents could also result in life-threatening side effects. For example, the use of interleukin-2 (IL-2) as an adjuvant greatly supports adoptive T cell therapy of melanoma, where IL-2 provides key adjuvant signals to transferred T cells but also elicits severe dose-limiting inflammatory toxicity and expands regulatory T cells (Tregs). One approach to focus adjuvant activity on the transferred cells is to genetically engineer the transferred cells to secrete their own supporting factors. The technical difficulty and challenges as well as the high cost for large-scale production of genetically engineered T lymphocytes have significantly limited the potential of this method in clinical applications, to date.

Disclosed herein, in some aspects, is a technology platform that permits simple, safe and efficient delivery of biologically-active agents, such as a drug, protein (e.g., adjuvants such as IL-2) or particle to cells through chemical conjugation of protein, drug, or particle-loaded, carrier-free linkers directly onto the plasma membrane of cells.

In addition to the foregoing, the present disclosure further contemplates other nanostructures that comprise other protein therapeutics for purposes other than adjuvant effect on adoptively-transferred cells. Those of skill in the art will readily recognize that the disclosure has broader applications, as provided herein.

Various aspects of the present disclosure may be used alone, in combination, or in a variety of arrangements not specifically discussed in the embodiments described in the foregoing and is therefore not limited in its application to the details and arrangement of components set forth in the foregoing description or illustrated in the drawings. For example, aspects described in one embodiment may be combined in any manner with aspects described in other embodiments.

Definitions

For convenience, certain terms employed in the specification, examples, and appended claims are collected here.

Unless defined otherwise, all technical and scientific terms used herein have the same meaning as commonly understood by one of ordinary skill in the art to which this disclosure belongs.

As used herein, the articles "a" and "an" refer to one or more than one, e.g., to at least one, of the grammatical object of the article. The use of the words "a" or "an" when used in conjunction with the term "comprising" herein may mean "one," but it is also consistent with the meaning of "one or more," "at least one," and "one or more than one."

As used herein, "about" and "approximately" generally mean an acceptable degree of error for the quantity measured given the nature or precision of the measurements. Exemplary degrees of error are within 20 percent (%), typically, within 10%, and more typically, within 5% of a given range of values. The term "substantially" means more than 50%, preferably more than 80%, and most preferably more than 90% or 95%.

As used herein the term "comprising" or "comprises" is used in reference to compositions, methods, and respective component(s) thereof, that are present in a given embodiment, yet open to the inclusion of unspecified elements.

As used herein the term "consisting essentially of" refers to those elements required for a given embodiment. The term permits the presence of additional elements that do not materially affect the basic and novel or functional characteristic(s) of that embodiment of the disclosure.

The term "consisting of" refers to compositions, methods, and respective components thereof as described herein, which are exclusive of any element not recited in that description of the embodiment.

As used herein, "a plurality of" means more than 1, e.g., 2, 3, 4, 5, 6, 7, 8, 9, 10, 11, 12, 13, 14, 15, 16, 17, 18, 19, 20, or more, e.g., 25, 30, 40, 50, 60, 70, 80, 90, 100, 200, 300, 400, 500, or more, or any integer therebetween.

The term "therapeutic," "therapeutic agent," "active," "active agent," "active pharmaceutical agent," "active drug" or "drug" as used herein means any active pharmaceutical ingredient ("API"), including its pharmaceutically acceptable salts (e.g. the hydrochloride salts, the hydrobromide salts, the hydroiodide salts, and the saccharinate salts), as well as in the anhydrous, hydrated, and solvated forms, in the form of prodrugs, and in the individually optically active enantiomers of the API as well as polymorphs of the API. Therapeutic agents include pharmaceutical, chemical or biological agents. Additionally, pharmaceutical, chemical or biological agents can include any agent that has a desired property or affect whether it is a therapeutic agent. For example, agents also include diagnostic agents, biocides and the like.

The terms "protein", "peptide" and "polypeptide" are used interchangeably herein to refer to polymers of amino acids of any length. The polymer may be linear or branched, it may comprise modified amino acids, and it may be interrupted by non-amino acids. The terms also encompass an amino acid polymer that has been modified; for example, disulfide bond formation, glycosylation, lipidation, acetylation, phosphorylation, or any other manipulation, such as conjugation with a labeling component. The polypeptide can be isolated from natural sources, can be a produced by recombinant techniques from a eukaryotic or prokaryotic host, or can be a product of synthetic procedures. It should be understood that the term "protein" includes fusion or chimeric proteins, as well as cytokines, antibodies and antigen-binding fragments thereof.

"Antibody" or "antibody molecule" as used herein refers to a protein, e.g., an immunoglobulin chain or fragment thereof, comprising at least one immunoglobulin variable domain sequence. An antibody molecule encompasses antibodies (e.g., full-length antibodies) and antibody fragments. In an embodiment, an antibody molecule comprises an antigen binding or functional fragment of a full length antibody, or a full length immunoglobulin chain. For example, a full-length antibody is an immunoglobulin (Ig) molecule (e.g., IgG) that is naturally occurring or formed by normal immunoglobulin gene fragment recombinatorial processes). In embodiments, an antibody molecule refers to an immunologically active, antigen-binding portion of an immunoglobulin molecule, such as an antibody fragment. An antibody fragment, e.g., functional fragment, is a portion of an antibody, e.g., Fab, Fab', F(ab')$_2$, F(ab)$_2$, variable fragment (Fv), domain antibody (dAb), or single chain variable fragment (scFv). A functional antibody fragment binds to the same antigen as that recognized by the intact (e.g., full-length) antibody. The terms "antibody fragment" or "functional fragment" also include isolated fragments consisting of the variable regions, such as the "Fv" fragments consisting of the variable regions of the heavy and light chains or recombinant single chain polypeptide molecules in which light and heavy variable regions are connected by a peptide linker ("scFv proteins"). In some embodiments, an antibody fragment does not include portions of antibodies without antigen binding activity, such as Fc fragments or single amino acid residues. Exemplary antibody molecules include full length antibodies and antibody fragments, e.g., dAb (domain antibody), single chain, Fab, Fab', and F(ab')$_2$ fragments, and single chain variable fragments (scFvs). The terms "Fab" and "Fab fragment" are used interchangeably and refer to a region that includes one constant and one variable domain from each heavy and light chain of the antibody, i.e., $V_L$, $C_L$, $V_H$, and $C_H1$.

In embodiments, an antibody molecule is monospecific, e.g., it comprises binding specificity for a single epitope. In some embodiments, an antibody molecule is multispecific, e.g., it comprises a plurality of immunoglobulin variable domain sequences, where a first immunoglobulin variable domain sequence has binding specificity for a first epitope and a second immunoglobulin variable domain sequence has binding specificity for a second epitope. In some embodiments, an antibody molecule is a bispecific antibody molecule. "Bispecific antibody molecule" as used herein refers to an antibody molecule that has specificity for more than one (e.g., two, three, four, or more) epitope and/or antigen.

"Antigen" (Ag) as used herein refers to a macromolecule, including all proteins or peptides. In some embodiments, an antigen is a molecule that can provoke an immune response, e.g., involving activation of certain immune cells and/or antibody generation. Antigens are not only involved in antibody generation. T cell receptors also recognized antigens (albeit antigens whose peptides or peptide fragments are complexed with an MEW molecule). Any macromolecule, including almost all proteins or peptides, can be an antigen. Antigens can also be derived from genomic recombinant or DNA. For example, any DNA comprising a nucleotide sequence or a partial nucleotide sequence that encodes a protein capable of eliciting an immune response encodes an "antigen." In embodiments, an antigen does not need to be encoded solely by a full length nucleotide sequence of a gene, nor does an antigen need to be encoded by a gene at all. In embodiments, an antigen can be synthesized or can be derived from a biological sample, e.g., a tissue sample, a tumor sample, a cell, or a fluid with other biological components. As used, herein a "tumor antigen" or interchangeably, a "cancer antigen" includes any molecule present on, or associated with, a cancer, e.g., a cancer cell or a tumor microenvironment that can provoke an immune response. As used, herein an "immune cell antigen" includes any molecule present on, or associated with, an immune cell that can provoke an immune response.

The "antigen-binding site" or "antigen-binding fragment" or "antigen-binding portion" (used interchangeably herein) of an antibody molecule refers to the part of an antibody molecule, e.g., an immunoglobulin (Ig) molecule such as IgG, that participates in antigen binding. In some embodiments, the antigen-binding site is formed by amino acid residues of the variable (V) regions of the heavy (H) and light (L) chains. Three highly divergent stretches within the variable regions of the heavy and light chains, referred to as hypervariable regions, are disposed between more conserved flanking stretches called "framework regions" (FRs). FRs are amino acid sequences that are naturally found between, and adjacent to, hypervariable regions in immunoglobulins. In embodiments, in an antibody molecule, the three hypervariable regions of a light chain and the three hypervariable regions of a heavy chain are disposed relative to each other in three dimensional space to form an antigen-binding surface, which is complementary to the three-dimensional surface of a bound antigen. The three hypervariable regions of each of the heavy and light chains are referred to as "complementarity-determining regions," or "CDRs." The framework region and CDRs have been defined and described, e.g., in Kabat, E. A., et al. (1991) Sequences of Proteins of Immunological Interest, Fifth Edition, U.S. Department of Health and Human Services, NIH Publication No. 91-3242, and Chothia, C. et al. (1987) J. Mol. Biol. 196:901-917. Each variable chain (e.g., variable heavy chain and variable light chain) is typically made up of three CDRs and four FRs, arranged from amino-terminus to carboxy-terminus in the amino acid order: FR1, CDR1, FR2, CDR2, FR3, CDR3, and FR4. Variable light chain (VL) CDRs are generally defined to include residues at positions 27-32 (CDR1), 50-56 (CDR2), and 91-97 (CDR3). Variable heavy chain (VH) CDRs are generally defined to include residues at positions 27-33 (CDR1), 52-56 (CDR2), and 95-102 (CDR3). One of ordinary skill in the art would understand that the loops can be of different length across antibodies and the numbering systems such as the Kabat or Chotia control so that the frameworks have consistent numbering across antibodies.

In some embodiments, the antigen-binding fragment of an antibody (e.g., when included as part of a fusion molecule) can lack or be free of a full Fc domain. In certain embodiments, an antibody-binding fragment does not include a full IgG or a full Fc but may include one or more constant regions (or fragments thereof) from the light and/or heavy chains. In some embodiments, the antigen-binding fragment can be completely free of any Fc domain. In some embodiments, the antigen-binding fragment can be substantially free of a full Fc domain. In some embodiments, the antigen-binding fragment can include a portion of a full Fc domain (e.g., CH2 or CH3 domain or a portion thereof). In some embodiments, the antigen-binding fragment can include a full Fc domain. In some embodiments, the Fc domain is an IgG domain, e.g., an IgG1, IgG2, IgG3, or IgG4 Fc domain. In some embodiments, the Fc domain comprises a CH2 domain and a CH3 domain.

As used herein, a "cytokine molecule" refers to full length, a fragment or a variant of a naturally-occurring, wild type cytokine (including fragments and functional variants thereof having at least 10% of the activity of the naturally-occurring cytokine molecule). In embodiments, the cytokine molecule has at least 30, 50, or 80% of the activity, e.g., the immunomodulatory activity, of the naturally-occurring molecule. In embodiments, the cytokine molecule further comprises a receptor domain, e.g., a cytokine receptor domain, optionally, coupled to an immunoglobulin Fc region. In other embodiments, the cytokine molecule is coupled to an immunoglobulin Fc region. In other embodiments, the cytokine molecule is coupled to an antibody molecule (e.g., an immunoglobulin Fab or scFv fragment, a Fab fragment, a FAB$_2$ fragment, or an affibody fragment or derivative, e.g., a sdAb (nanobody) fragment, a heavy chain antibody fragment, single-domain antibody, a bi-specific or multispecific antibody), or non-antibody scaffolds and antibody mimetics (e.g., lipocalins (e.g., anticalins), affibodies, fibronectin (e.g., monobodies or Adnectins), knottins, ankyrin repeats (e.g., DARPins), and A domains (e.g., avimers)).

The following definitions for certain chemical groups are used, unless otherwise described. Specific and general values listed below for radicals, substituents, and ranges, are for illustration only; they do not exclude other defined values or other values within defined ranges for the radicals and substituents. Unless otherwise indicated, alkyl, alkoxy, alkenyl, and the like denote both straight and branched groups.

The term "alkyl" refers to a saturated hydrocarbon chain that may be a straight chain or branched chain, containing the indicated number of carbon atoms. For example, $C_{1-6}$ alkyl indicates that the group may have 1 to 6 (inclusive) carbon atoms in it. Any atom can be optionally substituted, e.g., by one or more substituents. Examples of alkyl groups include without limitation methyl, ethyl, n-propyl, isopropyl, and tort-butyl.

As referred to herein, the term "alkoxy" refers to a group of formula —O(alkyl). Alkoxy can be, for example, methoxy (—OCH$_3$), ethoxy, propoxy, isopropoxy, butoxy, iso-butoxy, sec-butoxy, pentoxy, 2-pentoxy, 3-pentoxy, or hexyloxy. As used herein, the term "hydroxyl," employed alone or in combination with other terms, refers to a group of formula —OH.

The term "alkenyl" refers to a straight or branched hydrocarbon chain containing the indicated number of carbon atoms and having one or more carbon-carbon double bonds. Any atom can be optionally substituted, e.g., by one or more substituents. Alkenyl groups can include, e.g., vinyl, allyl, 1-butenyl, and 2-hexenyl. One of the double bond carbons can optionally be the point of attachment of the alkenyl substituent.

The term "alkynyl" refers to a straight or branched hydrocarbon chain containing the indicated number of carbon atoms and having one or more carbon-carbon triple bonds. Alkynyl groups can be optionally substituted, e.g., by one or more substituents. Alkynyl groups can include, e.g., ethynyl, propargyl, and 3-hexynyl. One of the triple bond carbons can optionally be the point of attachment of the alkynyl substituent.

The term "heterocyclyl" refers to a fully saturated monocyclic, bicyclic, tricyclic or other polycyclic ring system having one or more constituent heteroatom ring atoms independently selected from O, N (it is understood that one or two additional groups may be present to complete the nitrogen valence and/or form a salt), or S. The heteroatom or ring carbon can be the point of attachment of the heterocyclyl substituent to another moiety. Any atom can be optionally substituted, e.g., by one or more substituents. Heterocyclyl groups can include, e.g., tetrahydrofuryl, tetrahydropyranyl, piperidyl (piperidino), piperazinyl, morpholinyl (morpholino), pyrrolinyl, and pyrrolidinyl. By way of example, the phrase "heterocyclic ring containing from 5-6 ring atoms, wherein 1-2 of the ring atoms is independently selected from N, NH, N(C$_1$-C$_6$ alkyl), NC(O)(C$_1$-C$_6$ alkyl), O, and S; and wherein said heterocyclic ring is optionally substituted with 1-3 independently selected R$^a$" would include (but not be limited to) tetrahydrofuryl, tetrahydropyranyl, piperidyl (piperidino), piperazinyl, morpholinyl (morpholino), pyrrolinyl, and pyrrolidinyl.

The term "cycloalkyl" refers to a fully saturated monocyclic, bicyclic, tricyclic, or other polycyclic hydrocarbon groups. Any atom can be optionally substituted, e.g., by one or more substituents. A ring carbon serves as the point of attachment of a cycloalkyl group to another moiety. Cycloalkyl moieties can include, e.g., cyclopropyl, cyclobutyl, cyclopentyl, cyclohexyl, cycloheptyl, adamantyl, and norbornyl (bicycle[2.2.1]heptyl).

The term "aryl" refers to an aromatic monocyclic; bicyclic (2 fused rings), or tricyclic fused rings), or polycyclic (>3 fused rings) hydrocarbon ring system. One or more ring atoms can be optionally substituted, e.g., by one or more substituents. Aryl moieties include, e.g., phenyl and naphthyl.

The term "heteroaryl" refers to an aromatic monocyclic, bicyclic (2 fused rings), tricyclic (3 fused rings), or polycyclic (>3 fused rings) hydrocarbon groups having one or more heteroatom ring atoms independently selected from O, N (it is understood that one or two additional groups may be present to complete the nitrogen valence and/or form a salt), or S. One or more ring atoms can be optionally substituted, e.g., by one or more substituents. Examples of heteroaryl groups include, but are not limited to, 2H-pyrrolyl. 3H-indolyl, acridinyl, benzo[b]thienyl, benzothiazolyl, P-carbolinyl, carbazolyl, coumarinyl, chromenyl, cinnolinyl, dibenzo[b,d]furanyl, furazanyl, furyl, imidazolyl, imidazolyl, indazolyl, indolyl, isobenzofuranyl, isoindolyl, isoquinolyl, isothiazolyl, isoxazolyl, naphthyridinyl, oxazolyl, perimidinyl, phenanthridinyl, phenanthrolinyl, phenarsazinyl, phenazinyl, phenothiazinyl, phenoxathiinyl, phenoxazinyl, phthalazinyl, pteridinyl, purinyl, pyranyl, pyrazinyl, pyrazolyl, pyridazinyl, pyridyl, pyrimidinyl, pyrrolyl, quinazolinyl, quinolyl, quinoxalinyl, thiadiazolyl, thianthrenyl, thiazolyl, thienyl, triazolyl, and xanthenyl.

The term "substituent" refers to a group "substituted" on, e.g., an alkyl, haloalkyl, cycloalkyl, heterocyclyl, heterocycloalkenyl, cycloalkenyl, aryl, or heteroaryl group at any atom of that group. In one aspect, the substituent(s) on a group are independently any one single, or any combination of two or more of the permissible atoms or groups of atoms delineated for that substituent. In another aspect, a substituent may itself be substituted with any one of the above substituents. Further, as used herein, the phrase "optionally substituted" means unsubstituted (e.g., substituted with an H) or substituted. As used herein, the term "substituted" means that a hydrogen atom is removed and replaced by a substituent. It is understood that substitution at a given atom is limited by valency.

Various aspects of the disclosure are described in further detail below. Additional definitions are set out throughout the specification.

Linkers

In some embodiments, at least one drug, protein, polymer and/or particle (collectively, "agents") of the present disclosure are reversibly linked to one another through a degradable linker such that under physiological conditions, the linker degrades and releases the intact, biologically-active agent. In an embodiment, protein monomers can be cross-linked together to form a cluster that contains a plurality of the protein monomers. In other embodiments, various agents are linked to functional groups through a degradable linker. In various embodiments, the agents are reversibly modified or linked, as described below.

An agent that is "reversibly linked to another" agent, as used herein, refers to a drug, protein, polymer or particle that is attached (e.g., covalently attached) to another drug, protein, polymer or particle through a degradable linker.

An agent that is "reversibly linked to a functional group," or an agent that is "reversibly modified," herein refers to an agent that is attached (e.g., covalently attached) to a functional group through a degradable linker. Such an agent may be referred to herein as an "agent conjugate" or a "reversibly modified agent conjugate"—the terms may be used interchangeably herein. It should be understood that proteins and polymers (e.g., polyethylene glycol) each contain functional groups to which an agent can be linked via a reversible linker, such as amine, silane, hydroxyl, poly(ethylene oxide), polylactic acid, poly(lactic-co-glycolic acid), etc. Examples of agent conjugates and reversibly modified proteins, as provided herein, include without limitation, an agent reversibly linked (e.g., via a degradable linker) to another agent, an agent reversibly linked to a polymer, and a protein reversibly linked to another functional group. It should be understood that the term "protein" includes fusion proteins.

An example of a degradable linker for use in accordance with the present disclosure is represented by formula (I):

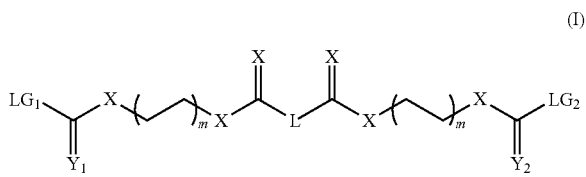

wherein:
LG$_1$ and LG$_2$ are each a leaving group, preferably independently selected from triflate, tosyl, Cl, N-hydroxysuccinimide and imidazolide;
Y$_1$ and Y$_2$ are each independently selected from O and S;
X, at each occurrence, is independently selected from O, S, and N;
L is a linkage such that

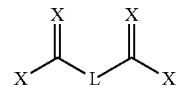

is biodegradable; and
m, at each occurrence, is an integer selected from 1-6.

In some embodiments, the compound represented by formula (I) is symmetrical at L. For example, LG$_1$ and LG$_2$ can be the same. Y$_1$ and Y$_2$ can be the same.

In various embodiments, LG$_1$ and LG$_2$ may be capable of reacting with a protein, a drug and/or a particle. LG$_1$ and LG$_2$ can both be imidazolide. In another example, LG$_1$ and LG$_2$ are both N-hydroxysuccinimide.

In certain embodiments,

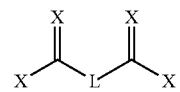

is hydrolysable. L can be selected from:
(a) —(CH$_2$)$_n$— wherein n is an integer selected from 0-5;

(b)

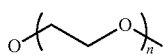

wherein n is an integer selected from 0-5; or (c)
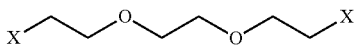

wherein X, at each occurrence, is independently selected from O, S, and N.

Another example of a degradable linker for use in accordance with the present disclosure is represented by formula (II):

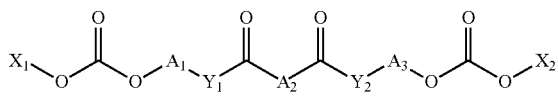

wherein:

$X_1$ and $X_2$ are each independently selected from triflate, tosyl, Cl, N-hydroxysuccinimide and imidazolide:

$A_1$ and $A_3$ are each independently —$(CR^1R^2)_n$—;

$A_2$ is —$(CR^1R^2)_m$—;

$Y_1$ and $Y_2$ are each independently selected from $NR^3$, O and S;

wherein $R^1$ and $R^2$ at each occurrence are independently selected from hydrogen, halogen, hydroxyl, $C_{1-12}$ alkyl, $C_{2-12}$ alkenyl, $C_{3-12}$ cycloalkyl, $C_{2-12}$ heterocyclyl; $C_{6-12}$ aryl optionally substituted with 1 or more halo, hydroxyl, $C_{1-6}$ alkyl and/or $C_{1-6}$ alkoxyl; and $C_{4-12}$ heteroaryl optionally substituted with 1 or more halo, hydroxyl, $C_{1-6}$ alkyl and/or $C_{1-6}$ alkoxyl wherein $R^3$ is selected from hydrogen, $C_{1-12}$ alkyl, $C_{2-12}$ alkenyl, $C_{3-12}$ cycloalkyl, $C_{2-12}$ heterocyclyl; $C_{6-12}$ aryl optionally substituted with 1 or more halo, hydroxyl, $C_{1-6}$ alkyl and/or $C_{1-6}$ alkoxyl; and $C_{4-12}$ heteroaryl optionally substituted with 1 or more halo, hydroxyl, $C_{1-6}$ alkyl and/or $C_{1-6}$ alkoxyl;

n, at each occurrence, is an integer independently selected from 1-12; and m is an integer selected from 0-12.

In some embodiments, the compound represented by formula (II) is symmetrical.

In some embodiments, $X_1$ and $X_2$ are each a leaving group capable of reacting with a protein, a drug and/or a particle. In certain embodiments, $X_1$ and $X_2$ are both imidazolide or N-hydroxysuccinimide.

In some embodiments, $R^1$ and $R^2$ are both hydrogen.

In some embodiments, $A_1$ and $A_3$ are both —$(CH_2)_2$—.

In certain embodiments, $A_2$ is —$(CH_2)_2$—.

In some embodiments, $Y_1$ and $Y_2$ are both O.

In some embodiments, the compound is:

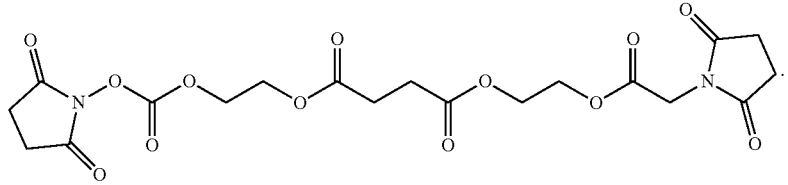 [SMILES: O=C(CCC(=O)OCCOC(=O)ON1C(=O)CCC1=O)OCCOC(=O)CN1C(=O)CCC1=O]

In some embodiments, $A_2$ is a bond. In certain embodiments, $Y_1$ and $Y_2$ are both NH.

In some embodiments, the compound is:

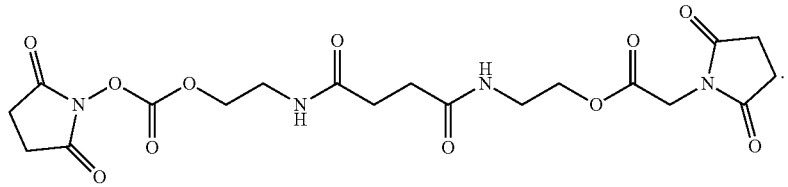 [SMILES: O=C(CCC(=O)NCCOC(=O)ON1C(=O)CCC1=O)NCCOC(=O)CN1C(=O)CCC1=O]

Use of Linkers

Examples of protein monomers for use in accordance with the present disclosure include, without limitation, antibodies (e.g., IgG, Fab, mixed Fc and Fab), single chain antibodies, antibody fragments, engineered proteins such as Fc fusions, enzymes, co-factors, receptors, ligands, transcription factors and other regulatory factors, cytokines, chemokines, human serum albumin, and the like. These proteins may or may not be naturally occurring. Other proteins are contemplated and may be used in accordance with the disclosure. Any of the proteins can be reversibly modified through cross-linking to form a cluster or nanogel structure as disclosed in, e.g., U.S. Publication No. 2017/0080104, U.S. Pat. No. 9,603,944, U.S. Publication No. 2014/0081012, and PCT Application No. PCT/US17/37249 filed Jun. 13, 2017, all incorporated herein by reference.

As illustrated in FIG. 1, two exemplary linkers, Linker-1 and Linker-2 can be used to cross-link various protein monomers having amine groups (represented by R—NH$_2$). Under suitable conditions, the disulfide bond in Linker-1 or the diester bond in Linker-2 can be hydrolyzed to release the original protein monomers to achieve, e.g., therapeutic effects.

In some embodiments, protein monomers of the disclosure are immunostimulatory proteins. As used herein, an immunostimulatory protein is a protein that stimulates an immune response (including enhancing a pre-existing immune response) in a subject to whom it is administered, whether alone or in combination with another protein or agent. Examples of immunostimulatory proteins that may be used in accordance with the disclosure include, without limitation, antigens, adjuvants (e.g., flagellin, muramyl dipeptide), cytokines including interleukins (e.g., IL-2, IL-7, IL-15, IL-10, IL-18, IL-21, IL-23 (or superagonist/mutant forms of these cytokines, such as, IL-15SA), IL-12, IFN-gamma, IFN-alpha, GM-CSF, FLT3-ligand), and immunostimulatory antibodies (e.g., anti-CTLA-4, anti-CD28, anti-CD3, or single chain/antibody fragments of these molecules). Other immunostimulatory proteins are contemplated and may be used in accordance with the disclosure. In some embodiments, the immunostimulatory proteins can be an antibody or antigen-binding fragment thereof that binds an inhibitor of an immunosuppressor, e.g., an inhibitor of a checkpoint inhibitor, such as PD-1, PD-L1, LAG-3, TIM-3, CTLA-4, inhibitory KIR, CD276, VTCN1, BTLA/HVEM, HAVCR2 and ADORA2A, e.g., as described in US 2016/0184399 incorporated herein by reference.

In some embodiments, protein monomers of the disclosure are antigens. Examples of antigens that may be used in accordance with the disclosure include, without limitation, cancer antigens, self-antigens, microbial antigens, allergens and environmental antigens. Other protein antigens are contemplated and may be used in accordance with the disclosure.

In some embodiments, proteins of the disclosure are cancer antigens. A cancer antigen is an antigen that is expressed preferentially by cancer cells (i.e., it is expressed at higher levels in cancer cells than on non-cancer cells) and, in some instances, it is expressed solely by cancer cells. Cancer antigens may be expressed within a cancer cell or on the surface of the cancer cell. Cancer antigens that may be used in accordance with the disclosure include, without limitation, MART-1/Melan-A, gp100, adenosine deaminase-binding protein (ADAbp), FAP, cyclophilin b, colorectal associated antigen (CRC)-0017-1A/GA733, carcinoembryonic antigen (CEA), CAP-1, CAP-2, etv6, AML1, prostate specific antigen (PSA), PSA-1, PSA-2, PSA-3, prostate-specific membrane antigen (PSMA), T cell receptor/CD3-zeta chain and CD20. The cancer antigen may be selected from the group consisting of MAGE-A1, MAGE-A2, MAGE-A3, MAGE-A4, MAGE-A5, MAGE-A6, MAGE-A7, MAGE-A8, MAGE-A9, MAGE-A10, MAGE-A11, MAGE-A12, MAGE-Xp2 (MAGE-B2), MAGE-Xp3 (MAGE-B3), MAGE-Xp4 (MAGE-B4), MAGE-C1, MAGE-C2, MAGE-C3, MAGE-C4 and MAGE-C5. The cancer antigen may be selected from the group consisting of GAGE-1, GAGE-2, GAGE-3, GAGE-4, GAGE-5, GAGE-6, GAGE-7, GAGE-8 and GAGE-9. The cancer antigen may be selected from the group consisting of BAGE, RAGE, LAGE-1, NAG, GnT-V, MUM-1, CDK4, tyrosinase, p53, MUC family, HER2/neu, p21ras, RCAS1, α-fetoprotein, E-cadherin, α-catenin, β-catenin, γ-catenin, p120ctn, gp100Pmel117, PRAME, NY-ESO-1, cdc27, adenomatous polyposis coli protein (APC), fodrin, Connexin 37, Ig-idiotype, p15, gp75, GM2 ganglioside, GD2 ganglioside, human papilloma virus proteins, Smad family of tumor antigens, Imp-1, P1A, EBV-encoded nuclear antigen (EBNA)-1, brain glycogen phosphorylase, SSX-1, SSX-2 (HOM-MEL-40), SSX-1, SSX-4, SSX-5, SCP-1 and CT-7, CD20 and c-erbB-2. Other cancer antigens are contemplated and may be used in accordance with the disclosure.

In some embodiments, proteins of the disclosure are antibodies or antibody fragments including, without limitation, bevacizumab (AVASTIN®), trastuzumab (HERCEPTIN®), alemtuzumab (CAMPATH®, indicated for B cell chronic lymphocytic leukemia), gemtuzumab (MYLOTARG®, hP67.6, anti-CD33, indicated for leukemia such as acute myeloid leukemia), rituximab (RITUXAN®), tositumomab (BEXXAR®, anti-CD20, indicated for B cell malignancy), MDX-210 (bispecific antibody that binds simultaneously to HER-2/neu oncogene protein product and type I Fc receptors for immunoglobulin G (IgG) (Fc gamma RI)), oregovomab (OVAREX®, indicated for ovarian cancer), edrecolomab (PANOREX®), daclizumab (ZENAPAX®), palivizumab (SYNAGIS®, indicated for respiratory conditions such as RSV infection), ibritumomab tiuxetan (ZEVALIN®, indicated for Non-Hodgkin's lymphoma), cetuximab (ERBITUX®), MDX-447, MDX-22, MDX-220 (anti-TAG-72), IOR-05, IOR-T6 (anti-CD1), IOR EGF/R3, celogovab (ONCOSCINT® OV103), epratuzumab (LYMPHOCIDE®), pemtumomab (THERAGYN®) and Gliomab-H (indicated for brain cancer, melanoma). Other antibodies and antibody fragments are contemplated and may be used in accordance with the disclosure.

Proteins may be linked (e.g., covalently linked) to a degradable linker through any terminal or internal nucleophilic groups such as a —NH$_2$ functional group (e.g., side chain of a lysine). For example, proteins can be contacted with a degradable linker under conditions that permit reversible covalent crosslinking of proteins to each other through the degradable linker. In some embodiments, the proteins can be cross-linked to form a plurality of protein nanogels. In some embodiments, the conditions include contacting the protein with the degradable linker in an aqueous buffer at a temperature of 4° C. to 25° C. In some embodiments, the contacting step can be performed in an aqueous buffer for 30 minutes to one hour. In some embodiments, the aqueous buffer comprises phosphate buffered saline (PBS). In some embodiments, the concentration of the protein in the aqueous buffer is 10 mg/mL to 50 mg/mL (e.g., 10, 5, 20, 25, 30, 35, 40, 45 or 50 mg/mL).

Cytokine Molecules

The methods and compositions, e.g., linker compounds, described herein can be used to cross-link one or more cytokine molecules. In embodiments, the cytokine molecule is full length, a fragment or a variant of a cytokine, e.g., a cytokine comprising one or more mutations. In some embodiments the cytokine molecule comprises a cytokine chosen from interleukin-1 alpha (IL-1 alpha), interleukin-1 beta (IL-1 beta), interleukin-2 (IL-2), interleukin-4 (IL-4), interleukin-5 (IL-5), interleukin-6 (IL-6), interleukin-7 (IL-7), interleukin-10 (IL-10), interleukin-12 (IL-12), interleukin-15 (IL-15), interleukin-17 (IL-17), interleukin-18 (IL-18), interleukin-21 (IL-21), interleukin-23 (IL-23), interferon (IFN) alpha, IFN beta, IFN gamma, tumor necrosis alpha, GM-CSF, GCSF, or a fragment or variant thereof, or a combination of any of the aforesaid cytokines. In other embodiments, the cytokine molecule is chosen from interleukin-2 (IL-2), interleukin-7 (IL-7), interleukin-12 (IL-12), interleukin-15 (IL-15), interleukin-18 (IL-18), interleukin-21 (IL-21), interleukin-23 (IL-23) or interferon gamma, or a fragment or variant thereof, or a combination of any of the aforesaid cytokines. The cytokine molecule can be a monomer or a dimer.

In embodiments, the cytokine molecule further comprises a receptor domain, e.g., a cytokine receptor domain. In one embodiment, the cytokine molecule comprises an IL-15 receptor, or a fragment thereof (e.g., an extracellular IL-15 binding domain of an IL-15 receptor alpha) as described herein. In some embodiments, the cytokine molecule is an IL-15 molecule, e.g., IL-15 or an IL-15 superagonist as described herein. As used herein, a "superagonist" form of a cytokine molecule shows increased activity, e.g., by at least 10%, 20%, 30%, compared to the naturally-occurring cytokine. An exemplary superagonist is an IL-15 SA. In some embodiments, the IL-15 SA comprises a complex of IL-15 and an IL-15 binding fragment of an IL-15 receptor, e.g., IL-15 receptor alpha or an IL-15 binding fragment thereof, e.g., as described herein.

In other embodiments, the cytokine molecule further comprises an antibody molecule, e.g., an immunoglobulin Fab or scFv fragment, a Fab fragment, a $FAB_2$ fragment, or an affibody fragment or derivative, e.g. a sdAb (nanobody) fragment, a heavy chain antibody fragment, e.g., an Fc region, single-domain antibody, a bi-specific or multispecific antibody). In one embodiment, the cytokine molecule further comprises an immunoglobulin Fc or a Fab.

In some embodiments, the cytokine molecule is an IL-2 molecule, e.g., IL-2 or IL-2-Fc. In other embodiments, a cytokine agonist can be used in the methods and compositions disclosed herein. In embodiments, the cytokine agonist is an agonist of a cytokine receptor, e.g., an antibody molecule (e.g., an agonistic antibody) to a cytokine receptor, that elicits at least one activity of a naturally-occurring cytokine. In embodiments, the cytokine agonist is an agonist of a cytokine receptor, e.g., an antibody molecule (e.g., an agonistic antibody) to a cytokine receptor chosen from an IL-15Ra or IL-21R.

In some embodiments, the cytokine molecule is an IL-15 molecule, e.g., a full length, a fragment or a variant of IL-15, e.g., human IL-15. In embodiments, the IL-15 molecule is a wild-type, human IL-15. In other embodiments, the IL-15 molecule is a variant of human IL-5, e.g., having one or more amino acid modifications. In some embodiments, the IL-15 molecule comprises a mutation, e.g., an N72D point mutation.

In other embodiments, the cytokine molecule further comprises a receptor domain, e.g., an extracellular domain of an IL-15R alpha, optionally, coupled to an immunoglobulin Fc or an antibody molecule. In embodiments, the cytokine molecule is an IL-15 superagonist (IL-15SA) as described in WO 2010/059253. In some embodiments, the cytokine molecule comprises IL-15 and a soluble IL-15 receptor alpha domain fused to an Fc (e.g., a sIL-15Ra-Fc fusion protein), e.g., as described in Rubinstein et al PNAS 103:24 p. 9166-9171 (2006).

The IL-15 molecule can further comprise a polypeptide, e.g., a cytokine receptor, e.g., a cytokine receptor domain, and a second, heterologous domain. In one embodiment, the heterologous domain is an immunoglobulin Fc region. In other embodiments, the heterologous domain is an antibody molecule, e.g., a Fab fragment, a $Fab_2$ fragment, a scFv fragment, or an affibody fragment or derivative, e.g. a sdAb (nanobody) fragment, a heavy chain antibody fragment. In some embodiments, the polypeptide also comprises a third heterologous domain. In some embodiments, the cytokine receptor domain is N-terminal of the second domain, and in other embodiments, the cytokine receptor domain is C-terminal of the second domain.

Certain cytokines and antibodies are disclosed in e.g., U.S. Publication No. 2017/0080104, U.S. Pat. No. 9,603,944, U.S. Publication No. 2014/0081012, and PCT Application No. PCT/US2017/037249 (each incorporated herein by reference in its entirety).

In some embodiments, the cytokines or other immunomodulators can target receptors (e.g., on an immune cell) by way of a fusion protein, such as those disclosed in PCT Application Nos. PCT/US2018/040777, PCT/US18/40783 and PCT/US18/40786 (each incorporated herein by reference in its entirety).

Backpacks and Cell Therapy

Figure 2:
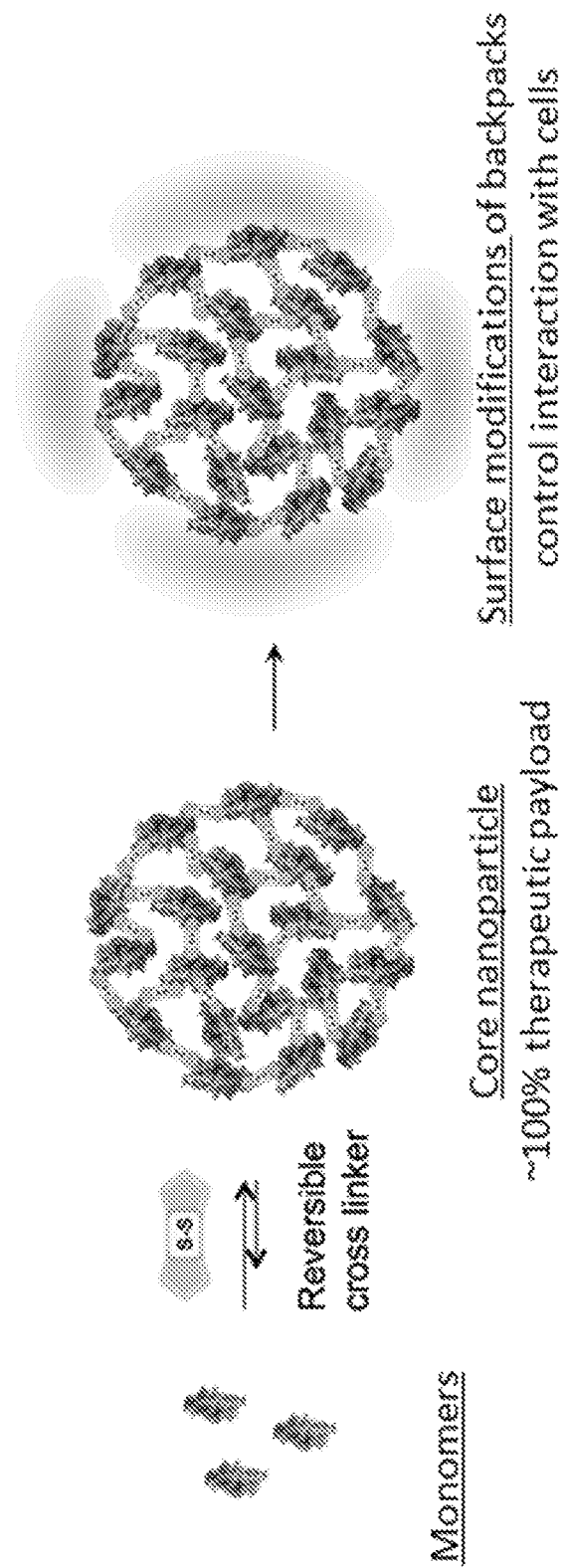
FIG. 2 shows that backpacks can be prepared by reacting various therapeutic protein monomers cross-linked using one or more cross-linkers disclosed herein.

Backpacks can be prepared by reacting various therapeutic protein monomers that can be cross-linked using one or more cross-linkers disclosed herein, as shown in FIG. 2. While FIG. 2 shows disulfide-containing linker for the purpose of illustration only, other biodegradable linkers disclosed herein can also be used.

In certain embodiments, the backpacks can be prepared by reacting the plurality of therapeutic protein monomers with the plurality of cross-linkers to form protein clusters having a size of, e.g., about 30 nm to 1000 nm in diameter. In some embodiments, the reaction can be performed at a temperature between about 5° C. and about 40° C. The reaction can be performed for about 1 minute to about 8 hours.

The protein clusters can be provided with a surface modification such as polycation (FIG. 2) so at to attach to cell surface which is negatively charged. Certain surface modification is disclosed in U.S. Publication No. 2017/0080104 and U.S. Pat. No. 9,603,944, both incorporated herein by reference in their entirety.

In some embodiments, the cross-linking reaction can proceed in the presence of one or more crowding agents such as polyethylene glycol (PEGs) and triglycerides. Exemplary PEGs include PEG400, PEG1000, PEG1500, PEG2000, PEG3000 and PEG4000.

Certain protein solubility aids such as glycerol, ethylene glycol and propylene glycol, Sorbitol and Mannitol can also improve the yield of backpack formation.

In certain embodiments, certain crosslinkers of the invention, due to the reaction of cationic lysine residues in the backpack, will result in a backpack having a net negative charge which will inhibit cell attachment. As such, it may be useful to first complex backpacks with a polycation via electrostatic interactions to drive cell attachment. For example, the backpacks can be coated or surface modified with a polycation such as polylysine (poly-L-lysine), polyethyleneimine, polyarginine, polyhistidine, polybrene and/ or DEAE-dextran. Polycation can help the backpacks nonspecifically bind or adsorb on cell membranes which are negatively charged. In some embodiments, polycation to be contained in a mixed solution may be a polymeric compound having a cationic group or a group that may become a cationic group, and an aqueous solution of a free polycation shows basic. Examples of the group that may become a cationic group include an amino group, an imino group, and the like. Examples of polycation include: polyamino acid such as polylysine, polyornithine, polyhistidine, polyarginine, polytryptophan, poly-2,4-diaminobutyric acid, poly-2,3-diaminopropionic acid, protamine, and polypeptide having at least one or more kinds of amino acid residues in a polypeptide chain selected from the group consisting of lysine, histidine, arginine, tryptophan, ornithine, 2,4-diaminobutyric acid and 2,3-diaminopropionic acid;

polyamine such as polyallylamine, polyvinylamine, a copolymer of allylamine and diallylamine, and polydiallylamine; and polyimine such as polyethyleneimine.

In some embodiments, the polycation coating or surface modifying agent used to promote backpack adhesion to the cell is a cationic block copolymer of PEG-polylysine such as [methoxy-poly(ethylene glycol)n-block-poly(L-lysine hydrochloride), PEG-polylysine] (PK30). This block copolymer may contain approximately 114 PEG units (MW approximately 5000 Da) and 30 lysine units (MW approximately 4900 Da). The linear PEG polymer has a methoxy end group, the poly-lysines are in the hydrochloride salt form. PK30 is a linear amphiphilic block copolymer which has a poly(L-lysine hydrochloride) block and a non-reactive PEG block. The poly-L-lysine block provides a net cationic charge at physiological pH and renders the backpack with a net positive charge after association. PK30 Structure [Methoxy-poly(ethylene glycol)n-block-poly(L-lysine hydrochloride)] is as follows.

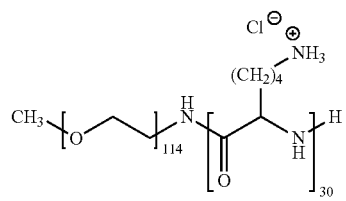

In some embodiments, the backpacks can be coated with an antibody or antigen-binding fragment thereof that bind to a receptor on the surface of an immune cell, so as to specifically target the backpacks to the immune cell. Exemplary antibodies include those disclosed herein, or fusion proteins containing the same.

Figure 3:
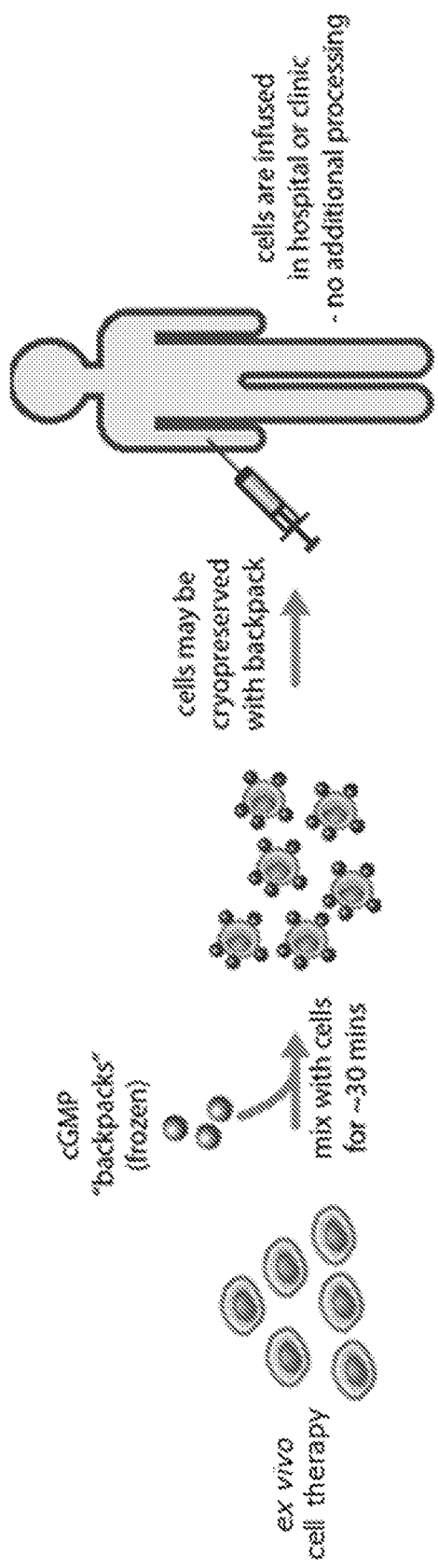
FIG. 3 shows an exemplary use of backpacks in cell therapy.

In some embodiments, once prepared and purified, the backpacks can be optionally frozen until use in cell therapy, as illustrated in FIG. 3.

For example, a cell therapy composition can be prepared by providing the protein clusters or backpacks disclosed herein, and incubating the protein clusters or backpacks with a nucleated cell such as T cell, B cell, natural killer (NK) cell and hematopoietic stem cell. T cells can include CD4+T cells, cytotoxic T cells (e.g., CD8+ T cells), alpha T cells, beta T cells, gamma T cells, delta T cells and regulatory T-cell (Tregs). In some embodiments, the nucleated cell (e.g., T cell or NK cell) may comprise, e.g., express, a Chimeric Antigen Receptor (CAR) such as a CAR that binds to a cancer antigen.

EXAMPLES

Example 1: Synthesis of Linker-1

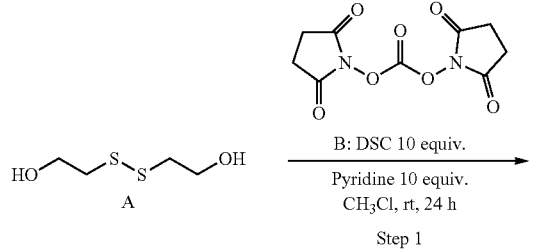

Step 1

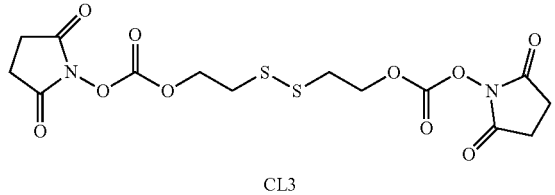

CL3

Carbonate Formation
A: 2,2'-disulfanediyldi(ethan-1-ol)(2.0 g, 1 equiv.)
B: DSC (N,N'-Disuccinimidyl carbonate) (33.2 g, 10.0 equiv.)
Pyridine (11.3 mL, 10.0 equiv.)
$CHCl_3$, r.t., 24 h
  (1) Stir a solution of 2,2'-disulfanediyldi (ethan-1-ol) (2.0 g, 12.98 mmol, 1 equiv.), in chloroform (333 mL, 165 V)
  (2) Add DSC (33.2 g, 12.98 mmol, 10.0 equiv.)
  (3) Add Pyridine (11.3 mL, 12.98 mmol, 10.0 equiv.)
  (4) Stir reaction mixture at room temperature for 24 h (TLC control)
  (5) Concentrate reaction mixture under reduced pressure to produce a semi solid
  (6) Dilute semi solid with ethyl acetate (200 mL) and wash with water (2×200 mL)
  (7) Concentrate the organic layer under reduced pressure to produce a white solid (2.4 g, impure)
  (8) Purify white solid by DCM to yield product (60% yield)
HPLC purity-96.75%. $^1$HNMR contains 1.63% DCM Example 2: Synthesis of Linker-2

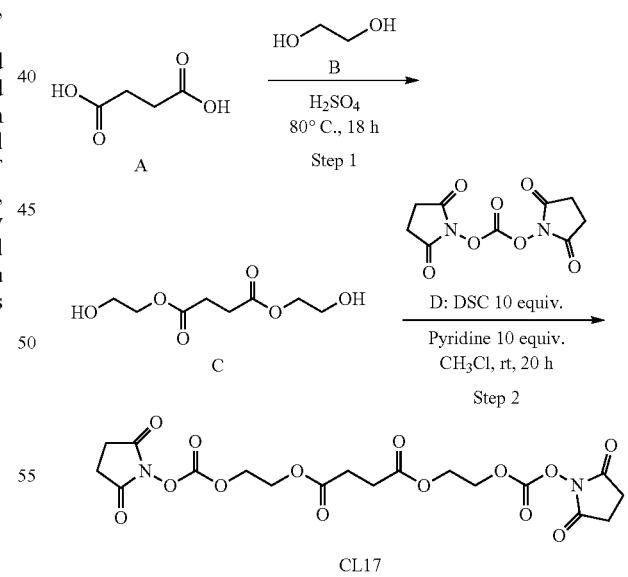

CL17

Step: 1 (Ester Formation)
A: Succinic acid (5.0 g, 1 equiv.)
B: Mono Ethylene Glycol (10 V)
$H_2SO_4$ (35 drops)
80° C., 18 h
  (1) To succinic acid (A) (5.0 g, 42.34 mmol, 1 equiv.) at room temperature (2) Add Mono Ethylene Glycol (B) (50 mL)
(3) Add $H_2SO_4$ (35 drops)
(4) Heat resulting reaction mixture to 80° C. for 18 h (TLC control)
(5) Cool to room temperature
(6) Neutralize with sodium bicarbonate (pH-7-8)
(7) Purify crude material by column chromatography; Elute desired compound with ethyl acetate
(8) Result is a colorless liquid C: (bis(2-hydroxyethyl) butanedioate) (3.96 g, 45.36% yield)

Step: 2 (Carbonate Formation)
C: Bis(2-hydroxyethyl) butanedioate (1.5 g, 1 equiv.)
D: DSC (18.66 g, 10 equiv.)
pyridine (5.76 g, 10 equiv.)
$CHCl_3$, r.t., 20 h
(1) Stir solution of bis(2-hydroxyethyl) butanedioate (C) (1.5 g, 1 equiv., 7.2 mmol) in $CHCl_3$ (150 mL, 100 V)
(2) Add DSC (D) (18.66 g, 72.74 mmol, 10 equiv.)
(3) Add pyridine (5.76 g, 72.74 mmol, 10 equiv.)
(4) Stir reaction mixture at room temperature for 20 h (TLC control)
(5) Concentrate reaction mixture under reduced pressure
(6) Dilute with DCM and wash with water (2×300 mL)
(7) Separate organic layer and dry over anhydrous sodium sulfate
(8) Concentrate under reduced pressure to produce 1.9 g off white semi solid,
(9) Lyophilize
(10) 1.9 g (impure) compound was triturated with DCM:Methanol to afford 1.06 g of off white solid

Example 3: IL-15 Backpacks Mediated Cell Expansion In Vitro

Protein nanogels comprising a crosslinked protein nanoparticle were formed as follows. IL-15 was crosslinked into protein nanogels by incubating the protein at a concentration of 17 mg/mL with a 27-fold molar excess of Linker-1 or Linker-2 in the presence of a final concentration of 2.5% polyethylene glycol with an average molecular weight of 400 Dalton (PEG-400, Spectrum Chemical Mfg. Corp.) and 10% glycerol (Sigma). After 30 minutes incubation at room temperature, the reactions were diluted with Dulbecco's phosphate buffered saline (DPBS) to a final cytokine concentration of 1.5 mg/mL. Protein nanogels were then purified from linker leaving groups (which comprise molecular fragments of the linker that are removed as part of the cross-linking reaction) and unreacted linker by buffer exchange into DPBS using a Zeba column (40,000 MW cut-off, Thermo-Fisher). Zeba columns were used according to the manufacturer's instructions, including equilibrating the column in DPBS by three consecutive washes with DPBS to facilitate buffer exchange, followed by application of the reaction products. Buffer-exchanged protein nanogels were analyzed by size exclusion chromatography (SEC) using a BioSep™ SEC-s4000 column (Phenomenex Inc.) with PBS (pH 7.2) as eluent (flow rate 0.5 mL/min) on a Prominence HPLC system equipped with a photodiode array (Shimadzu Corp.).

Protein nanogels at a cytokine concentration of approximately 1-1.5 mg/mL were conjugated with a polyethylene glycol-polylysine (PEG-polyK) block co-polymer: PEG5k-polyK30 (Alamanda Polymers cat. no. 050-KC030), which is a block co-polymer comprising a polyethylene glycol polymer of 5 kiloDalton (kD) average molecular weight and a 30 amino acid polylysine polymer (polylysine30 or polyK30). PEG5k-polyK30 or were reconstituted to 1 mg/mL in DPBS and added to 1-1.5 mg/mL of protein nanogels at a final block copolymer concentration of 50 ug/mL and incubated at room temperature for 30 min.

T cell expansion analysis. Protein nanogels comprising PEG5k-polyK30 at a protein concentration of 1-1.5 mg/mL were mixed in equal volume with $1\times10^6$ CD3+ T-cells in HBSS at a cell concentration of $100\times10^6$ cells/mL and incubated at 37° C. for 1 hr. T-cells were then washed three times with RPMI media containing 10% FBS, penicillin/streptomycin, and Glutamax (all from ThermoFisher Scientific, Inc.), seeded at a cell density of approximately $1\times10^6$ cells/mL, and cultured for 9 days in 24-well tissue culture plates. Cells were split into fresh medium at a ratio of 1:5 on three days after cell attachment of backpacks. Cell proliferation was measured by live-dead cell stain (7-AAD) and counting beads (CountBright Absolute Counting Beads, Thermo Fisher Scientific, Inc.) by flow cytometry on Days 0, 3, 6, 9, 12, 15.

Figure 4:
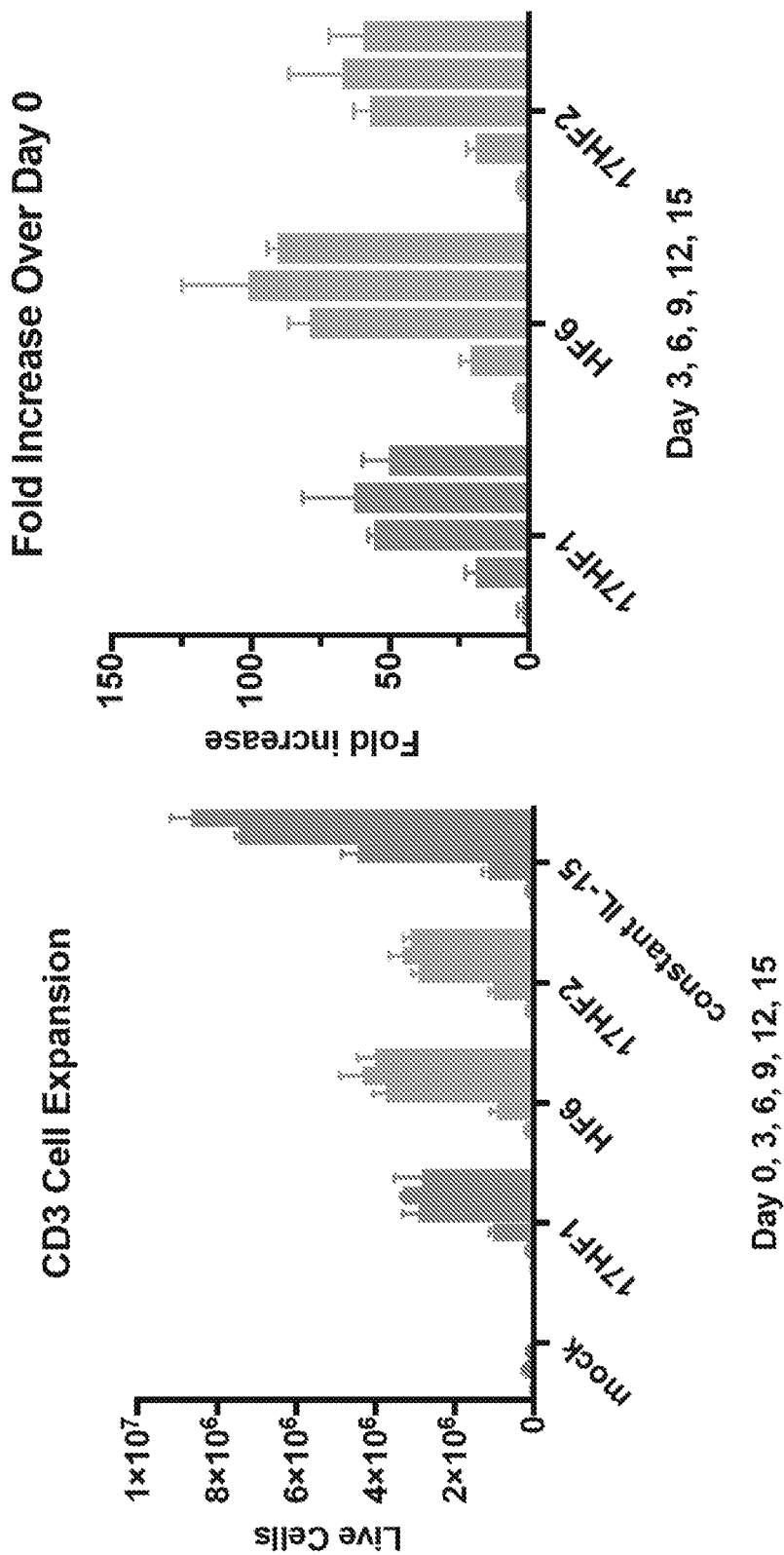
FIG. 4: Two Linker-2 cross-linked IL-15 backpack formulations (17HF1 and 17HF2) showed comparable cell expansion with a Linker-1 cross-linked IL-15 backpack formulation (HF6).

As shown in FIG. 4, two Linker-2 cross-linked IL-15 backpack formulations (17HF1 and 17HF2) showed comparable cell expansion with a Linker-1 cross-linked IL-15 backpack formulation (HF6). Mock is negative control with HBSS only.

Figure 5:
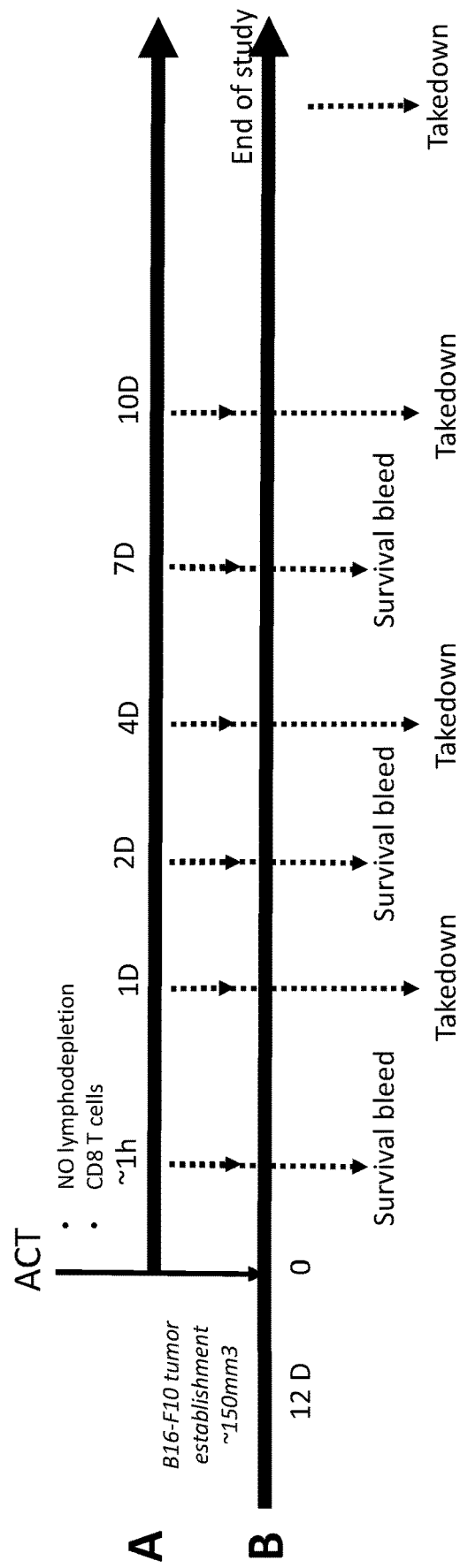
FIG. 5: Exemplary PMEL experimental outline.

Example 4: Comparison of Linker-1- and Linker-2-Crosslinked IL-15 Backpacks Using Pmel T Cells B16F10 murine melanoma cells were injected intra-dermally into the shaved flank of 6-week old C57BL/6 female mice ($10^5$ cells/mouse). After 7 days, Pmel transgenic CD8 T cells previously incubated with HBSS, IL15, Linker-1-IL15 backpack ("PMEL1" or "BP-Linker-1") or Linker-2-IL15 backpack ("PMEL2" or "BP-Linker-2") were dosed intravenously ($10^6$ cells/mouse). On day 5 or day 7, transferred T-cells in the blood were counted by flow cytometry. Data are reported as number of donor CD8 T cells per ul of blood. Experimental outline is shown in FIG. 5. Treatment groups include:
1. Saline
2. PMEL T cells (10×10^6)
3. IL-015 (10 ug)+PMEL T cells (10×10^6) (separate injection)
4. TRQ-PMEL1 (10×10^6) (Linker-1 cross-linked IL-015; BP-Linker-1)
5. TRQ-PMEL2 (10×10^6) (Linker-2 cross-linked IL-015; BP-Linker-2)

Figure 6:
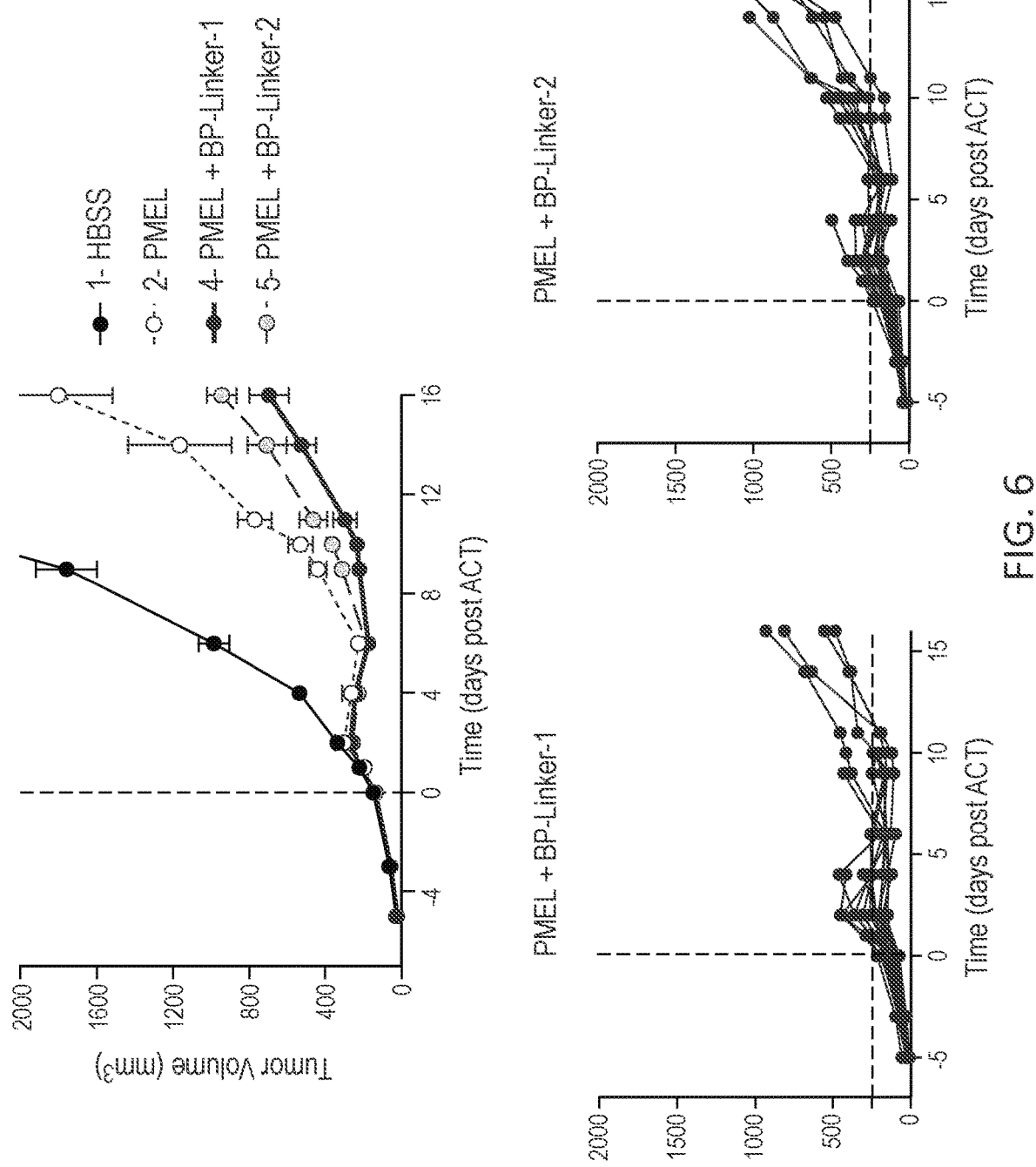
FIG. 6, BP-Linker-1 and BP-Linker-2 show similar anti-tumor activity in vivo. In addition, BP-Linker-1 and BP-Linker-2 show comparable distribution in the organs analyzed including blood, spleen, lung, and tumor (not shown).

Readouts include:
1. Flow for T cell expansion and phenotype (blood, tumor, spleen, draining lung)
2. IL-15 (TRQ-15A) content in blood and tissues (tumor, liver, spleen, lung, kidney; ELISA)
3. Complete Blood Counts (CBC; whole blood)
4. Blood chemistry (AST, ALT, . . . ; serum)
5. Cytokine release (Luminex/ELISA; serum)
6. Pathology review on histology (liver, spleen, lung, kidney, brain and tumor)
7. Tumor growth and changes in mouse weight As shown in FIG. 6, BP-Linker-1 and BP-Linker-2 show similar anti-tumor activity in vivo. In addition, BP-Linker-1 and BP-Linker-2 show comparable distribution in the organs analyzed including blood, spleen, lung, and tumor (not shown).

Figure 7:
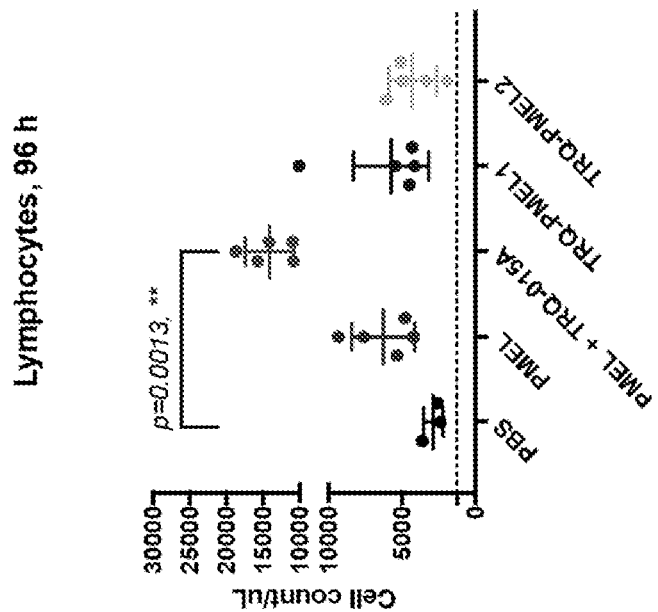
FIG. 7 shows that there are no significant effects on Complete Blood Counts (CBC) with BP-Linker-1 (TRQ-PMEL1) and BP-Linker-2 (TRQ-PMEL2) in either tumor or non tumor-bearing mice.
Figure 7:
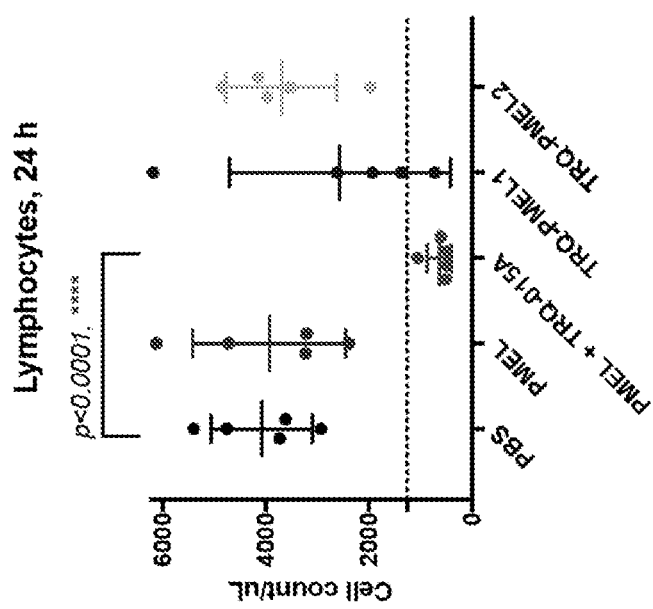

FIG. 7 shows that there are no significant effects on Complete Blood Counts (CBC) with BP-Linker-1 (TRQ-PMEL1) and BP-Linker-2 (TRQ-PMEL2) in either tumor or non tumor-bearing mice.

Figure 8:
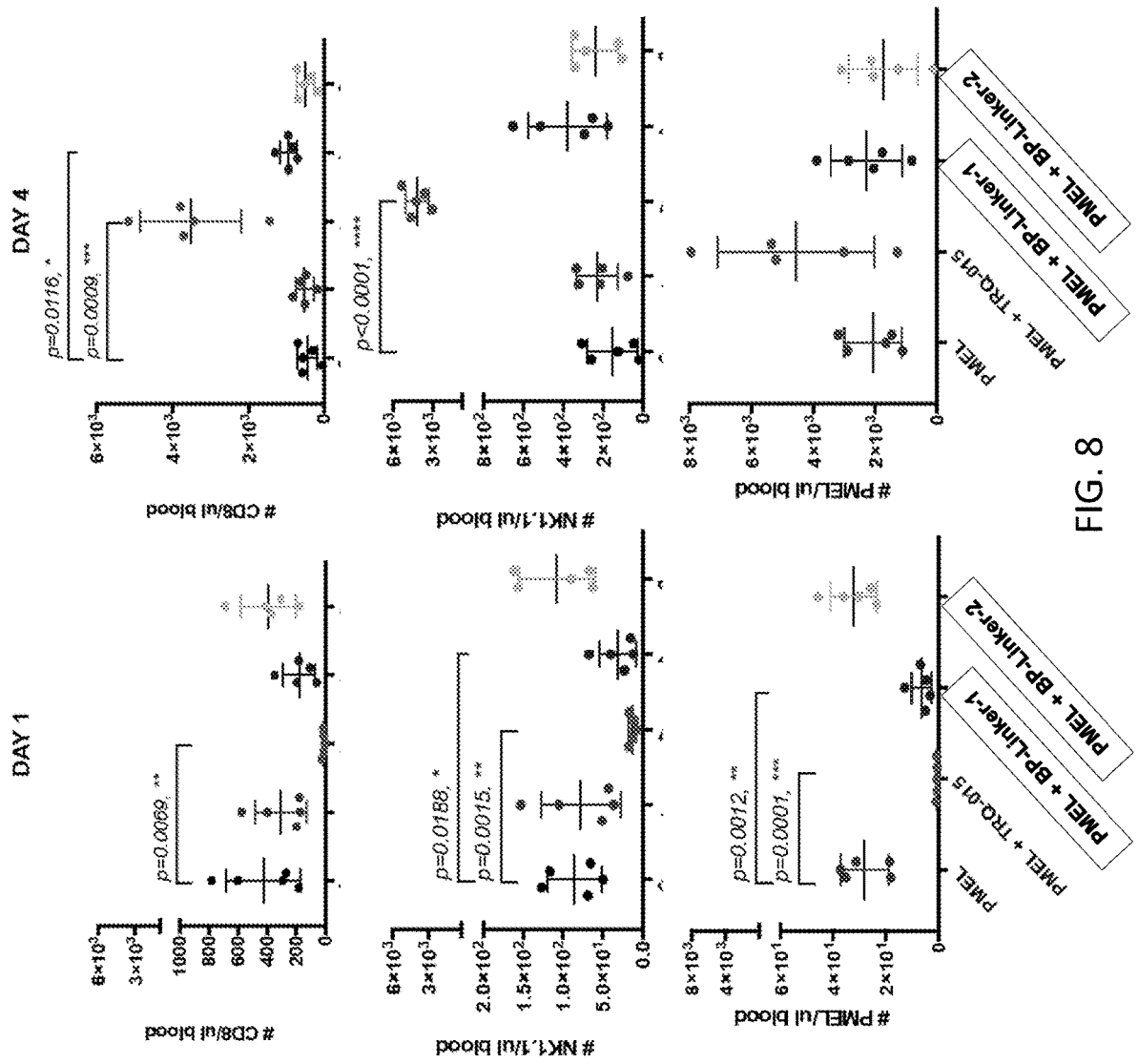
FIG. 8: BP-Linker-2 shows trends toward lower lymphodepletion (CD8, NK1.1 and transferred PMELs) compared to BP-Linker-1.

BP-Linker-2 shows trends toward lower lymphodepletion (CD8, NK1.1 and transferred PMELs) compared to BP-Linker-1 (FIG. 8).

Figure 9:
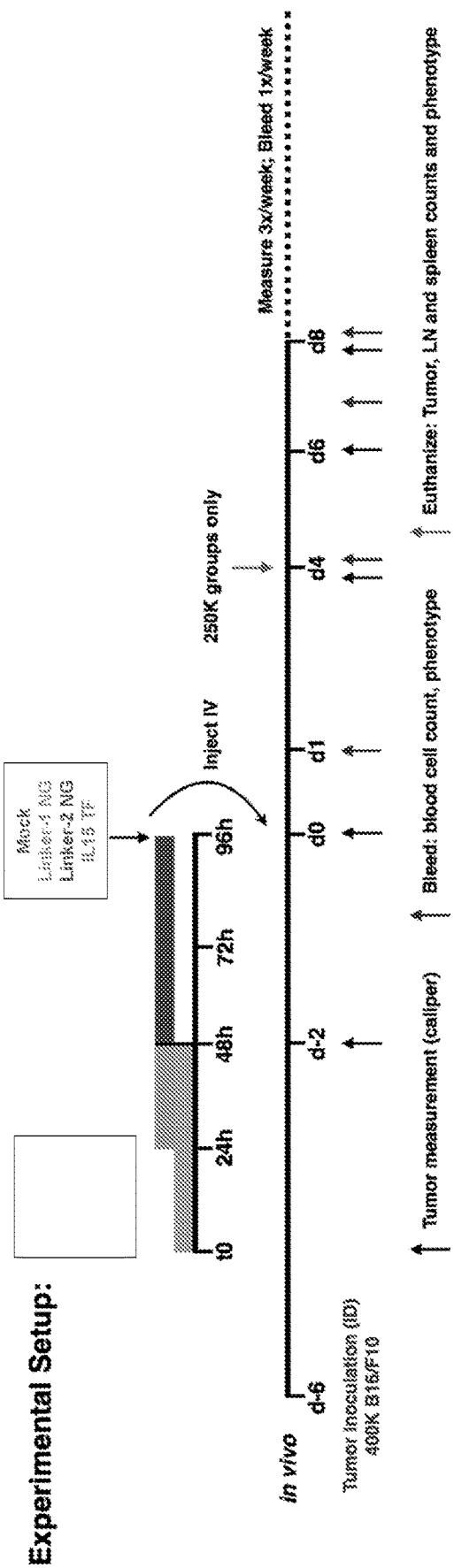
FIG. 9: Experimental outline of another set of PMEL study.

In another set of PMEL experiments outlined in FIG. 9, BP-Linker-1 (also referred to as "Linker-1 NG") and BP-Linker-2 (also referred to as "Linker-2 NG") were compared to a tethered fusion of anti-CD45 Fab and IL-15 ("IL15 TF"). Briefly, Pmel cells were grown according to standard protocols, and then backpacked with 1.5 mg/ml Linker-1 NG, Linker-2 NG or IL15 TF. Then the cells were resuspended at 12.5M/ml (2.5M/injection), and diluted 1:10 in HBSS for 250 k/ml injections. Tethered fusions are disclosed in PCT Application Nos. PCT/US2018/040777, PCT/US18/40783 and PCT/US18/40786 (each incorporated herein by reference in its entirety).

Figure 10:
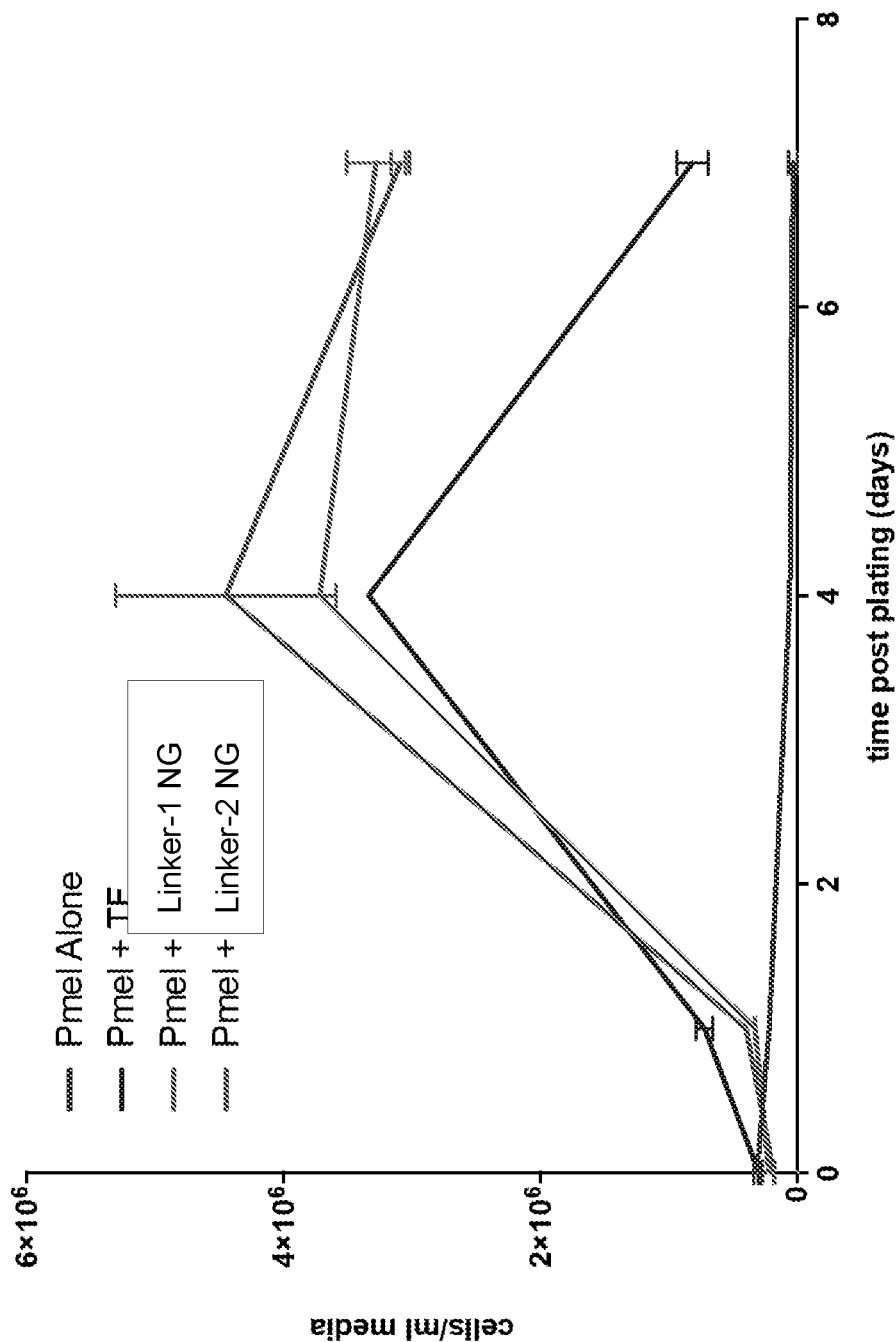
FIGS. 10 and 11 are the in vitro Pmel expansion curves by number of cells (FIG. 10) and present viable cells (FIG. 11).
Figure 11:
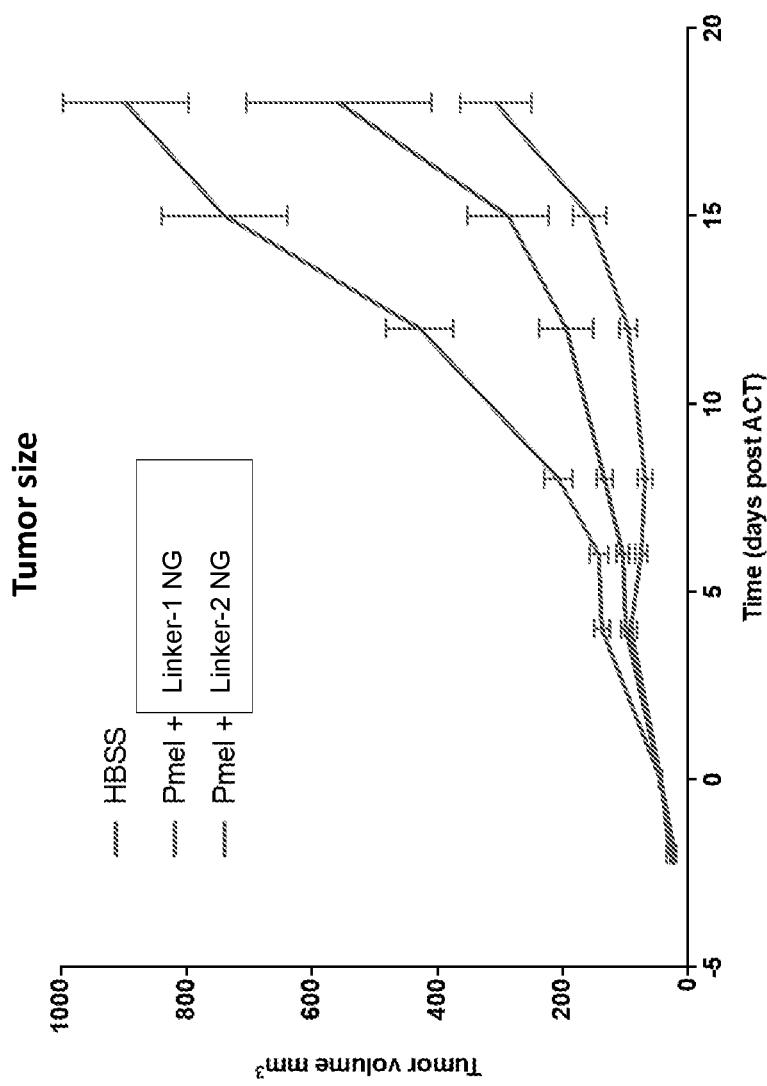
Figure 12:
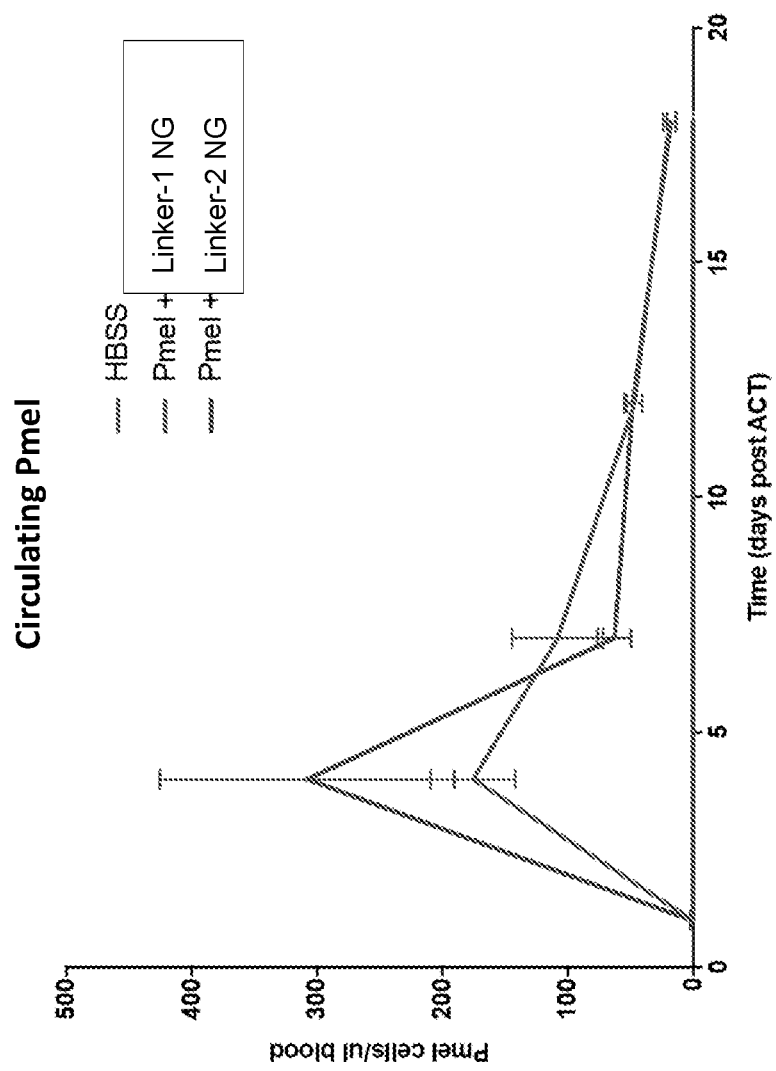
FIG. 12: Linker-1 NG and Linker-2 NG show comparable amount of circulating Pmel.
Figure 13:
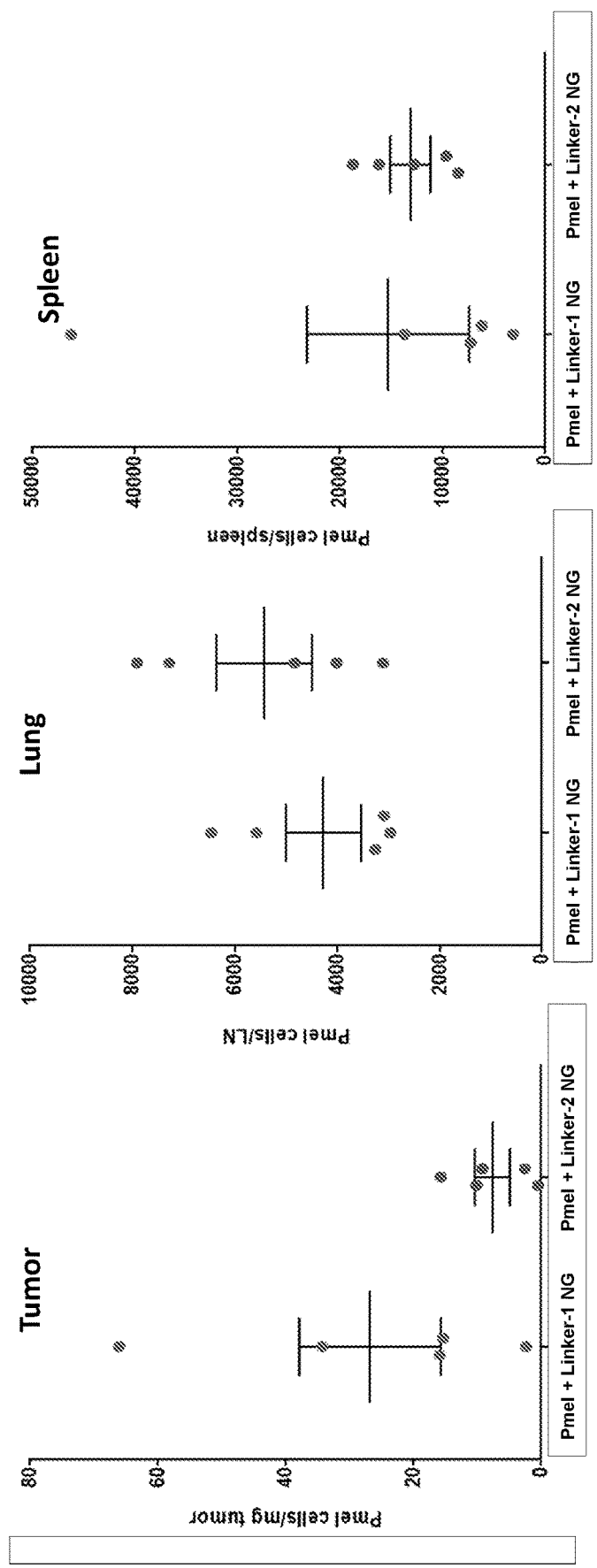
FIG. 13: Linker-1 NG and Linker-2 NG show comparable amount of tumor-infiltrating Pmel.
Figure 14:
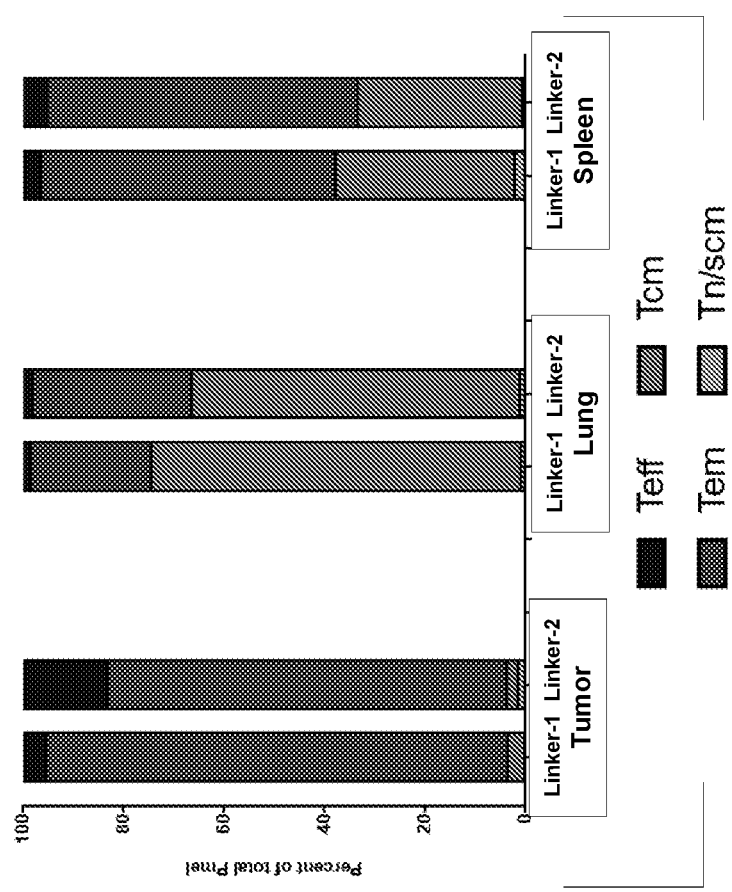
FIG. 14: Linker-2 backpacked Cells have older memory phenotype, with significant increase in Teff cells in Linker-2 relative to Linker-1 at d4 after injection. Tcm: central memory T cells; Teff: effector memory T cells; Temra: effector memory-RA+ T cells; Tscm: memory stem T cells; Tnaive: naïve T cells.

After backpack and wash, cells are counted, normalized and plated. After injection, plated cells are counted and cell number and viability determined. FIGS. 10 and 11 are the in vitro Pmel expansion curves by number of cells (FIG. 10) and present viable cells (FIG. 11). Without NG or TF, Pmel rapidly die in vitro. Linker-1 NG and Linker-2 NG have a slight lag in expansion relative to TF and then expand robustly. Despite being normalized for cell number at plating/injection, by 4 hours there are significantly more cells and a significant increase in viability for Linker-1 NG and Linker-2 NG backpacked cells relative to mock or TF backpacked cells In vivo data shows that Linker-1 NG and Linker-2 NG both displayed anti-tumor activity (FIG. 11) with comparable amount of circulating Pmel (FIG. 12) and comparable amount of tumor-infiltrating Pmel (FIG. 13). Linker-2 backpacked Cells have older memory phenotype, with significant increase in Teff cells in Linker-2 relative to Linker-1 at d4 after injection (FIG. 14). (Tcm: central memory T cells; Teff: effector memory T cells; Temra: effector memory-RA+ T cells; Tscm: memory stem T cells; Tnaive: naïve T cells.)

Example 5: Linker-1- and Linker-2-Crosslinked IL-15 Backpacks in CAR T Therapy

Figure 15:
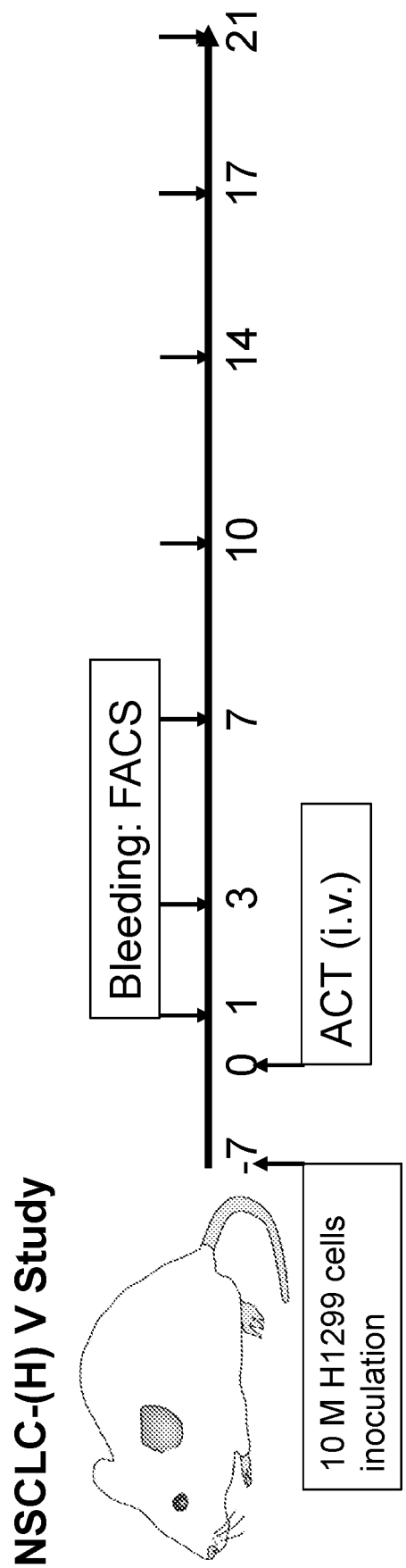
FIG. 15: Efficacy of backpacked Chimeric Antigen Receptor (CAR) T cells.

The efficacy of backpacked Chimeric Antigen Receptor (CAR) T cells was analyzed as outlined in FIG. 15:
Group 1: Untreated ("Mock")
Group 2: 5 M EGFR CAR CD3 T cells ("CAR")
Group 3: 5 M Linker-1-IL15 backpacked (75 μg, 1 hr) EGFR CAR CD3 T cells ("Linker-1-HF6")
Group 4: 5 M Linker-2-IL15 backpacked (75 μg, 1 hr) EGFR CAR CD3 T cells ("Linker-2-HF1")
Group 5: 5 M anti-CD45 Fab-IL15 tethered fusion (100 nM, 0.5 hr) EGFR CAR CD3 T cells ("TF" or "h9.4Fab-IL15")

Figure 16:
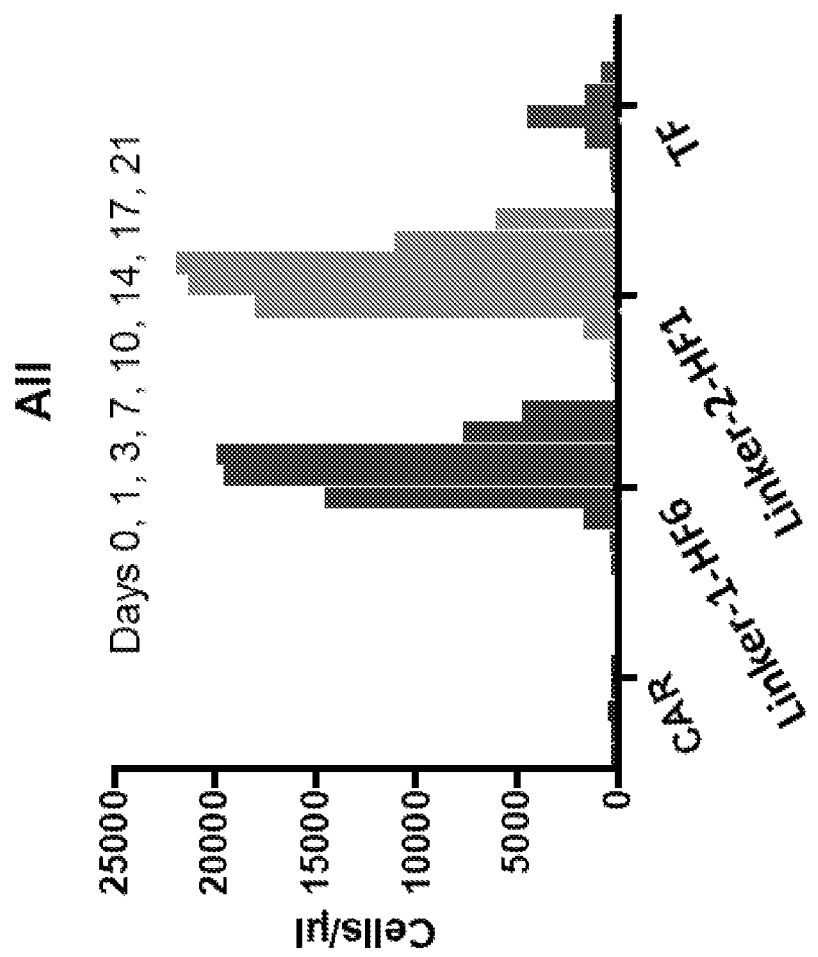
FIG. 16: In vitro proliferation on day 0, 1, 3, 7, 10, 14, 17 and 21 of CAR, Linker-1-HF6, Linker-2-HF1 and TF.
Figure 17:
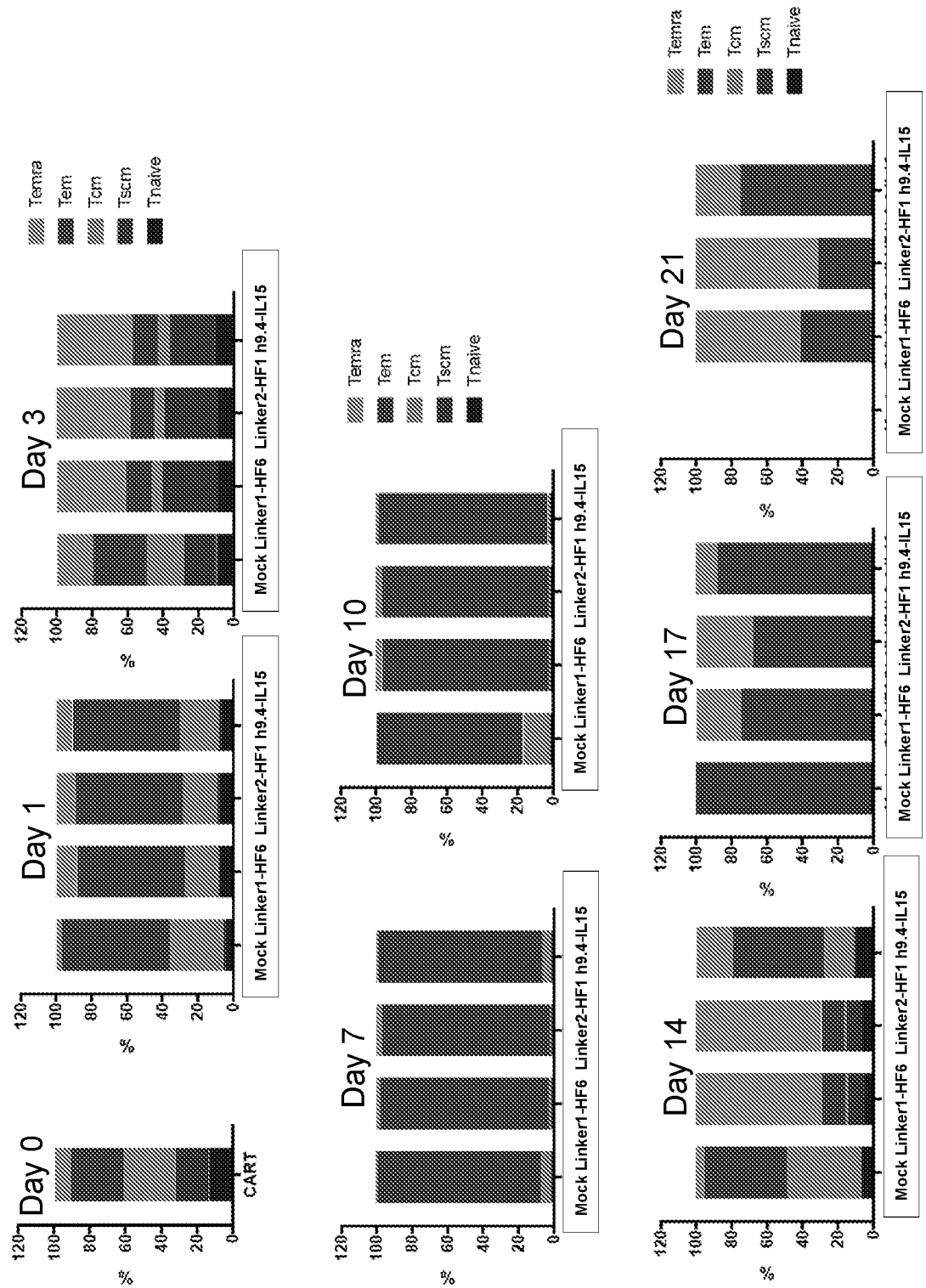
FIG. 17 shows phenotyping of the backpacked T cell groups described in FIG. 16 on days 0, 1, 3, 7, 10, 14, 17, and 21.

The in vitro proliferation on day 0, 1, 3, 7, 10, 14, 17 and 21 of CAR, Linker-1-HF6, Linker-2-HF1 and TF is shown in FIG. 16. Linker-1-HF6 and Linker-2-HF1 show comparable in vitro proliferation. Phenotyping of these cells over time is shown in FIG. 17. Again, Linker-1-HF6 and Linker-2-HF1 show comparable phenotypes.

Figure 18:
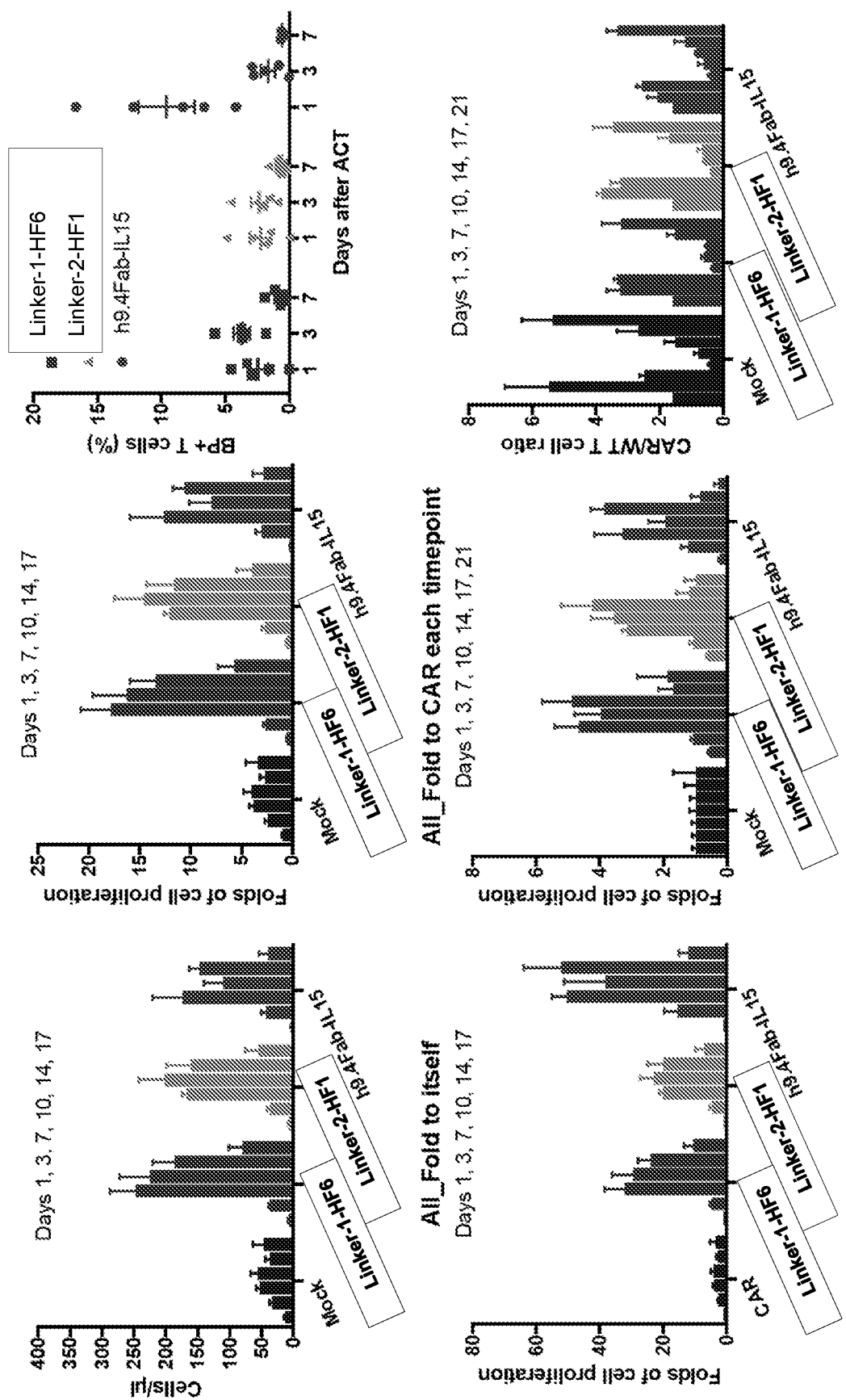
FIG. 18: Backpacked cells expanded significantly more compared to CAR alone or mock.
Figure 19A:
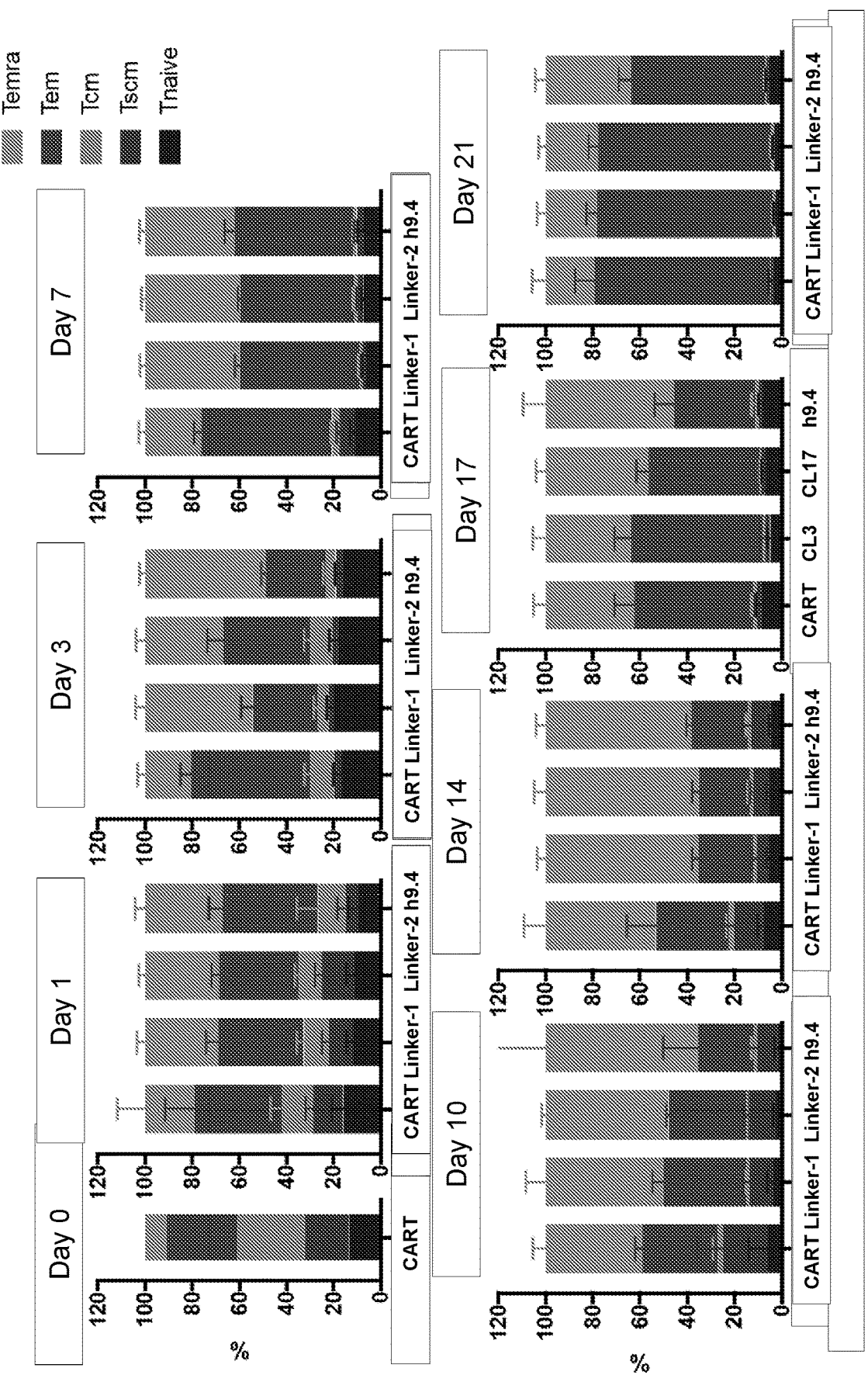
FIGS. 19A-19B: Phenotypes remain similar through day 21 for Tnaive, Tscm and Tcm, while Tem and Temra composition varied slightly (Tcm: central memory T cells; Tem: effector memory T cells; Temra: effector memory-RA+ T cells; Tscm: memory stem T cells; Tnaive: naïve T cells).
Figure 19B:
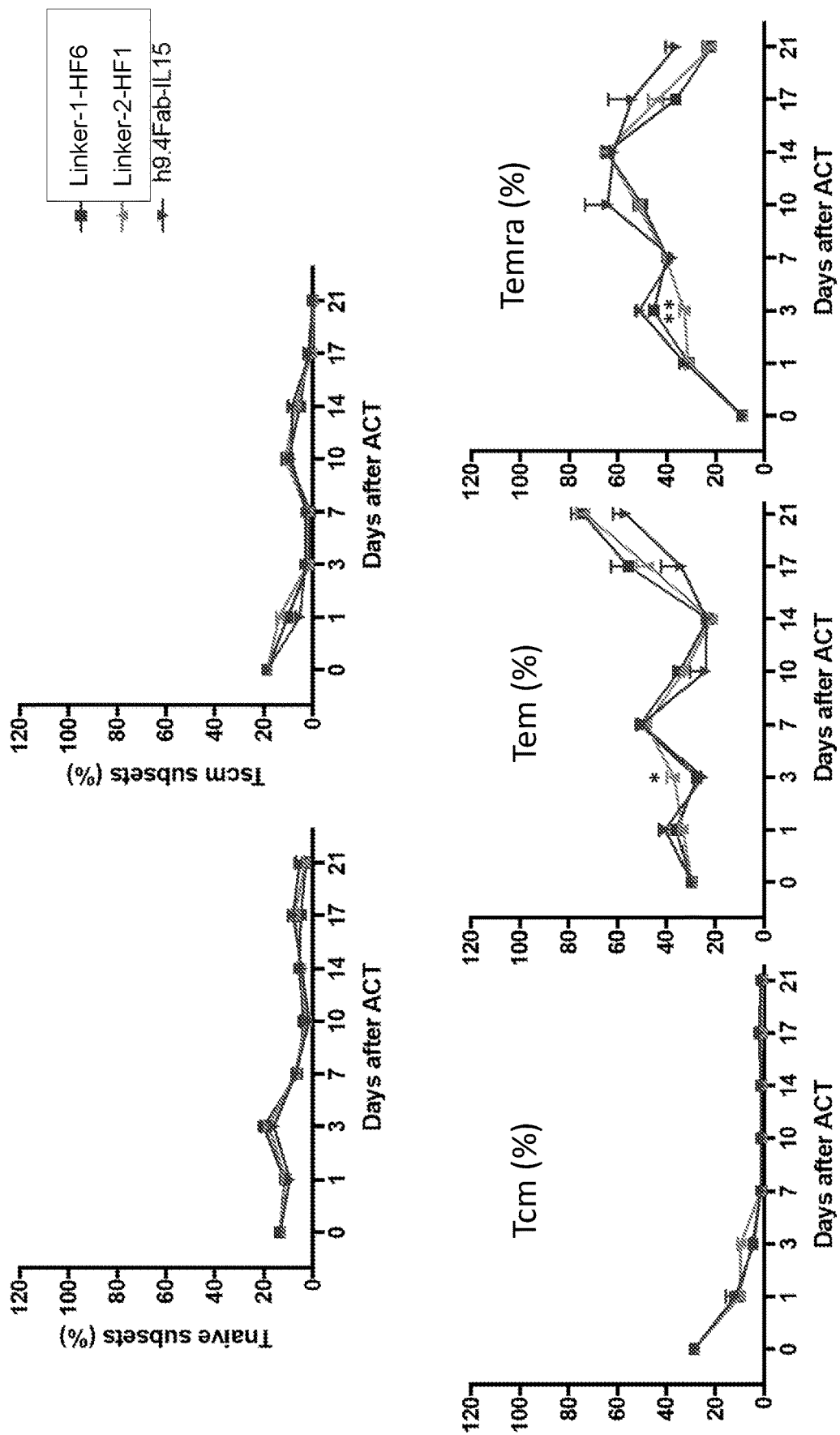

In vivo proliferation and phenotyping are shown in FIGS. 18 and 19A-19B, respectively. Backpacked cells expanded significantly more compared to CAR alone or mock (FIG. 18). Phenotypes remain similar through day 21 for Tnaive, Tscm and Tcm, while Tem and Temra composition varied slightly (FIGS. 19A-19B) (Tcm: central memory T cells; Tem: effector memory T cells; Temra: effector memory-RA+ T cells; Tscm: memory stem T cells; Tnaive: naïve T cells).

Figure 20:
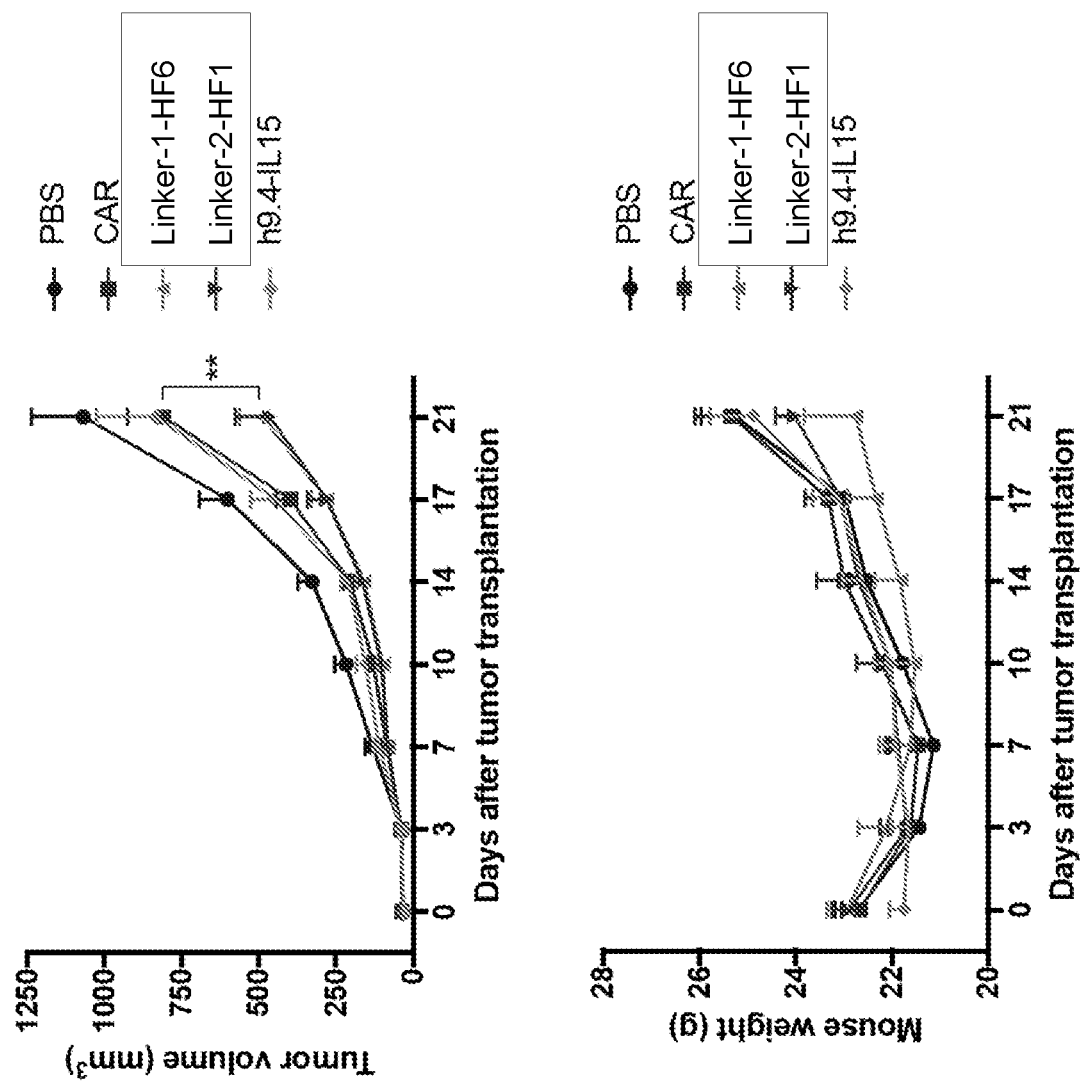
FIG. 20 shows the efficacy of backpacked CAR T treatment, as Linker-1-HF6 and Linker-2-HF1 both statistically significantly (as indicated by **) delayed/inhibited tumor growth compared to CAR alone or h9.4-IL15 backpack at all time points analyzed.
Figure 21:
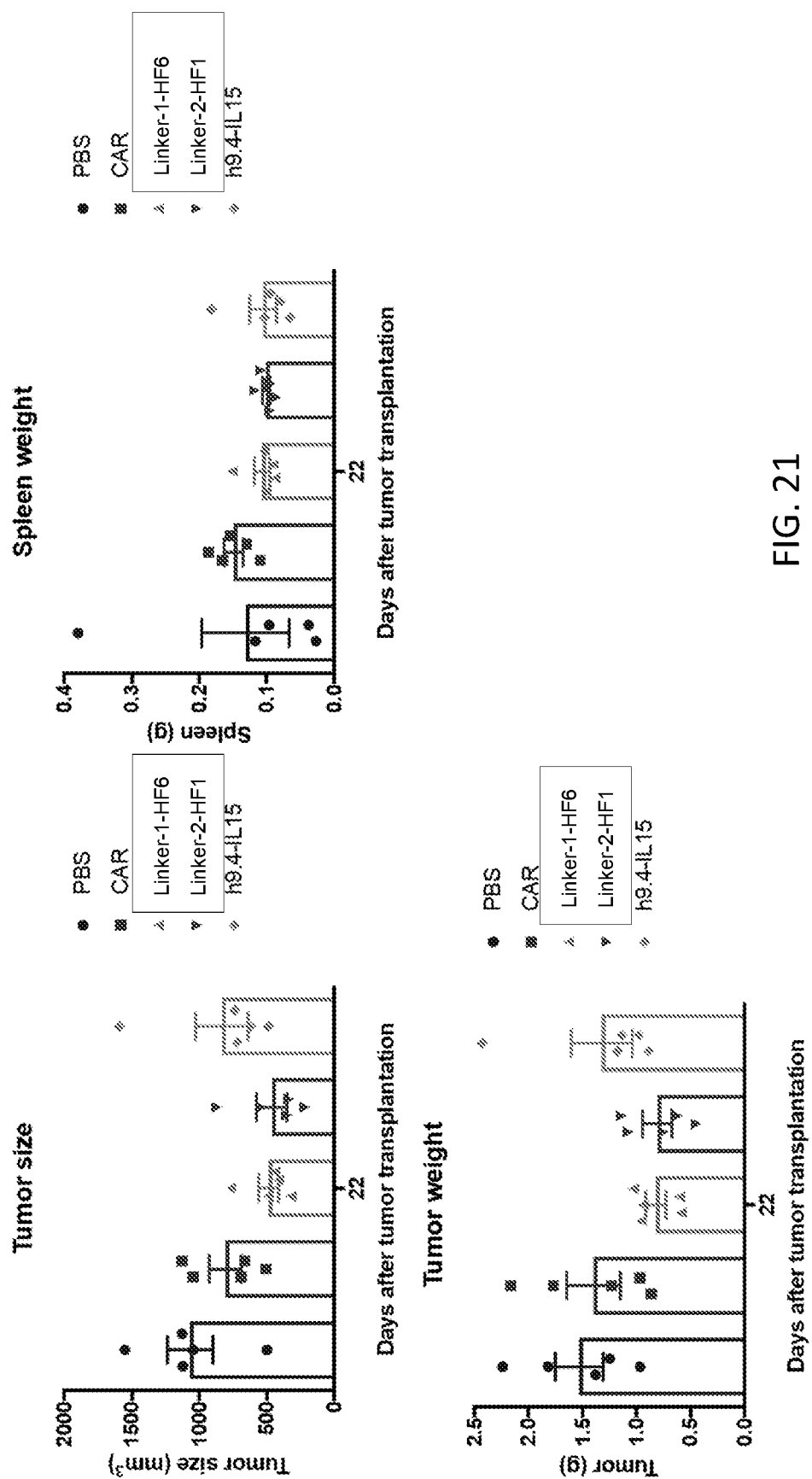
FIGS. 21 and 22: On day 22, tumor size, tumor weight, spleen weight, number of tumor-infiltrating lymphocytes (TILs), number of CAR TILs and TIL phenotype were also analyzed.
Figure 22:
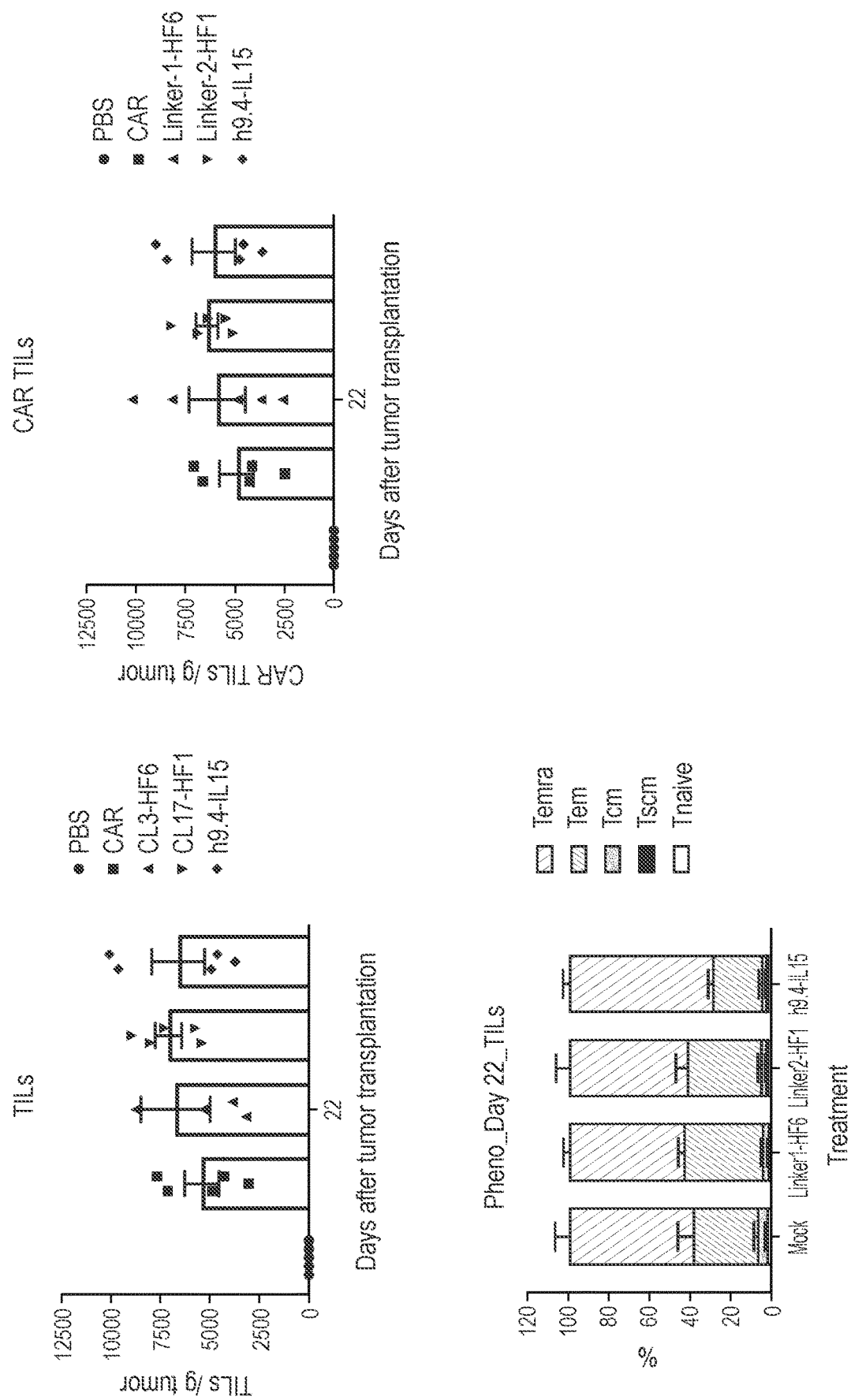

FIG. 20 shows the efficacy of backpacked CAR T treatment, as Linker-1-HF6 and Linker-2-HF1 both statistically significantly (as indicated by **) delayed/inhibited tumor growth compared to CAR alone or h9.4-IL15 backpack at all time points analyzed. On day 22, tumor size, tumor weight, spleen weight, number of tumor-infiltrating lymphocytes (TILs), number of CAR TILs and TIL phenotype were also analyzed (FIGS. 21 and 22).

In summary, both Linker-1- and Linker-2-backpacked CAR T cells showed enhanced T cell expansion in vivo, resulting in better therapeutic efficacy and tumor killing activity than non-backpacked CAR T cells. The folds of expanded CAR T induced by Linker-1 or Linker-2 are identical and 4-fold higher than non-backpacked CAR T cells. Linker-2 may slow down T cell differentiation at early time point, while having substantially the same outcome of tumor inhibition, compared to Linker-1. Tumor size is slightly correlated with spleen size, peripheral CAR T cells, proliferative tumor-infiltrating CAR T cells in 3-week treatment. Linker-1 and Linker-2 are comparable in in vitro proliferation and in vivo efficacy study.

Example 6: Pharmacological Activity of Deep IL-15 Primed PMEL T Cells

Deep IL-15 refers to a multimer of human IL-15 receptor α-sushi-domain-Fc fusion homodimers with two associated IL-15 molecules (IL15-Fc), connected by a cleavable cross-linker (Linker-2), and non-covalently coated with a poly-ethylene glycol (PEG)-polylysine$_{30}$ block copolymer (PK30). Specifically, Deep IL-15 is a multimer of human IL15-Fc monomers, connected by a hydrolysable crosslinker (CL17) and non-covalently coated with a polyethylene glycol (PEG)-polylysine$_{30}$ block copolymer (PK30). IL15-Fc monomers consist of two subunits, each consisting of an effector attenuated IgG2 Fc variant fused with an IL-15 receptor α-sushi-domain noncovalently bound to a molecule of IL-15. Deep IL-15 Primed T cells are generated via a loading process in which target cells are co-incubated with Deep IL-15 at high concentrations. Through this process, Deep IL-15 becomes associated with the cell via electrostatic interactions and is internalized to create intracellular reservoirs of Deep IL-15. From these reservoirs, Deep IL-15 slowly releases bioactive IL15-Fc by hydrolysis of the crosslinker. This extended release of IL15-Fc promotes proliferation and survival of Deep IL-15 Primed T cells, providing a targeted, controllable and time-dependent immune stimulus.

The objective of this study was to test the pharmacological activity of Deep IL-15 primed PMEL T cells in C57BL/6J mice with and without orthotopically placed B16-F10 melanoma tumors. Control groups included vehicle control, PMEL cells alone and PMEL cells+IL15-Fc, administered in a separate injection (10 maximum tolerated dose, MTD).
Materials and Methods
B16-F10 Tumor Establishment and Tumor Measurements B16-F10 melanoma tumor cells ($0.2 \times 10^6$) were injected intra-dermally into the shaved right flank of female C57BL/6 mice (Jackson Labs) on study day −12. The body weights were recorded and tumor dimensions (length [L] and width [W], defined in the list of abbreviations) were measured with calipers 2 to 3 times per week. Tumor volumes were calculated using the formula: $W^2 \times L \times \pi/6$.
Isolation and Expansion of PMEL Cells PMEL cells were isolated from the spleens and lymph nodes (inguinal, axillary and cervical) of 14 female transgenic PMEL mice (Jackson Laboratories, Bar Harbor, Me.). The spleens and lymph nodes were processed with a GentleMACS Octo Dissociator (Miltenyi Biotech, Auburn, Calif.) and passed through a 40 μm strainer. The cells were washed by centrifugation and the CD8a+ cells were purified using an IMACS naïve CD8a+ isolation kit (Miltenyi Biotech,) and a MultiMACS cell 24 block (Miltenyi Biotech) and separator (Miltenyi Biotech) with 18 columns following the manufacturer's protocol. The non-CD8a+ cells were removed by an affinity column and the CD8a+ T-cells were collected in the column eluate. The purity of CD8a+ cells was confirmed by flow cytometry.

Upon isolation (D0) purified CD8a+ cells from PMEL mice were plated into ten, 6-well tissue culture plates coated with anti-CD3 and anti-CD28 at a density of $5 \times 10^6$ cells/well and incubated for 24 hr at 37° C. and 5% CO2. Murine IL-2 (20 ng/mL) and murine IL-7 (0.5 ng/mL) were added 24 hr post plating (D1). On D2 and D3, the cells were counted and diluted to a concentration of $0.2 \times 10^6$ cells/mL with fresh media containing murine IL-21 (10 ng/mL). The cells were collected on D4 to obtain a total of $100 \times 10^6$ PMEL cells/mL in 28 mL of vehicle control.

Preparation of Deep IL-15 Primed PMEL T Cells

Five mL of PMEL cells ($100 \times 10^6$ cells/mL) were mixed with 5.5 mL of Deep IL-15 (1.36 mg/ml) and incubated with rotation for 1 hr at 37° C. to create Deep IL-15 Primed PMEL cells. Deep IL-15 Primed PMEL cells were washed (3×, first with medium and then twice with HBSS) by centrifugation (500 g) and counted. Deep IL-15 Primed PMEL cells were resuspended at a concentration of $50 \times 10^6$ cells/mL. The mice in Groups 5A and 5B were injected with 200 μL of this preparation for a total of $10 \times 10^6$ Deep IL-15 Primed PMEL cells per mouse. PMEL cells (15 mL at $100 \times 10^6$ cells/mL) were mixed with 15 mL of HBSS, incubated with rotation for 1 hr at 37° C., washed (3×, first with medium and then twice with HBSS) by centrifugation (500 g) and counted. PMEL cells were resuspended at a concentration of $50 \times 10^6$ cells/mL. The mice in Groups 2A and 2B were injected IV with 200 μL of this preparation for a total of $10 \times 10^6$ PMEL cells per mouse. The mice in Groups 3A and 3B were injected IV with 200 μL of this preparation for a total of $10 \times 10^6$ PMEL cells per mouse, and received a retro-orbital injection of IL15-Fc (10 μg/mouse in 50 μl HBSS; lot #TS0). Based on an average loading efficiency of 39%, the total amount of IL15-Fc associated with $10 \times 10^6$ PMEL cells is 58.5 μg, which is 5.85-fold higher than the amount delivered systemically by injection of IL15-Fc (10 μg) in Groups 3A and 3B.

Fc-IL-15 ELISA

An Fc-IL15 Enzyme-Linked Immunosorbent Assay (ELISA) was used to determine the IL15 Fc concentration in the samples collected at 2 hr, D1, 2, 4 and 10 post-dose. ELISA plates (were coated overnight at 4° C. with Goat Anti-human IgG Fc Capture Antibody. Plates were washed and blocked with reagent diluent for at least 2 hours at 30° C. Plates were washed, samples (diluted in reagent diluent) and IL15-Fc standards (in duplicate, 31 to 2000 pg/mL, in reagent diluent) were added to the wells, and plates were incubated for 1 hour at 37° C. Plates were washed followed by addition of biotin-anti-IL15 detection Antibody was added and incubated for 1 hour at 37° C. Plates were washed and incubated with Streptavidin-HRP for 20 min at 37° C. Plates were washed followed by addition of 3,3',5,5'-Tetramethylbenzidine (TMB) Substrate Solution and incubated for 20 min at room temperature in the dark until the reaction was stopped. Plates were read on a microplate reader (450 nm).

The assay was run twice. For the first run, samples were evaluated at the following dilutions: 1:20000 for the 2 hr time point, 1:5000 for the D1 time point, and 1:250 for the D2, D4 and D10 time points. For the second run, samples from groups 3A and 3B, were diluted 1:5000 for the D1 time point, 1:250 for the D2 time point and 1:25 for the D4 and D10 time points. Samples from groups 1A and 1B, 2A and 2B and 5A and 5B were diluted 1:25 for all the time points analyzed. The data is reported for the second run. However, because the samples for the 2 hr time point were exhausted for the second run, and given that IL15-Fc concentrations at 24 hr were similar in groups 3A and 3B across the two runs, the 2 hr values from the first run were included with the other data points from the second run for the purpose of calculating pharmacokinetic (PK) parameters.

The lower limit of quantitation (LLOQ) in blood was 310 ng/ml for the 1:20000 dilution, 77.5 ng/ml for the 1:5000 dilution, 3.875 ng/ml for the 1:250 dilution and 0.3875 ng/ml for the 1:25 dilution.

Serum Cytokine Levels in Serum from Mice

ThermoFisher ProcartaPlex mouse high sensitivity panel 5plex Cat. #EPXS0S0-22199-901 kits were used according to manufacturer's protocol and samples were analyzed on a Bio-Plex 200 system. Serum was thawed on ice, and 20 μL of serum were tested for IFN-γ, TNF-α, IL-2, IL-4 and IL-6 levels. In a few samples, 20 μL of serum were not available, so a smaller volume was utilized. Dilution factors were adjusted, to calculate concentrations according to the standard curves. Statistical analysis was carried out in GraphPad Prism.

Results

Clinical Chemistry

Figure 23:
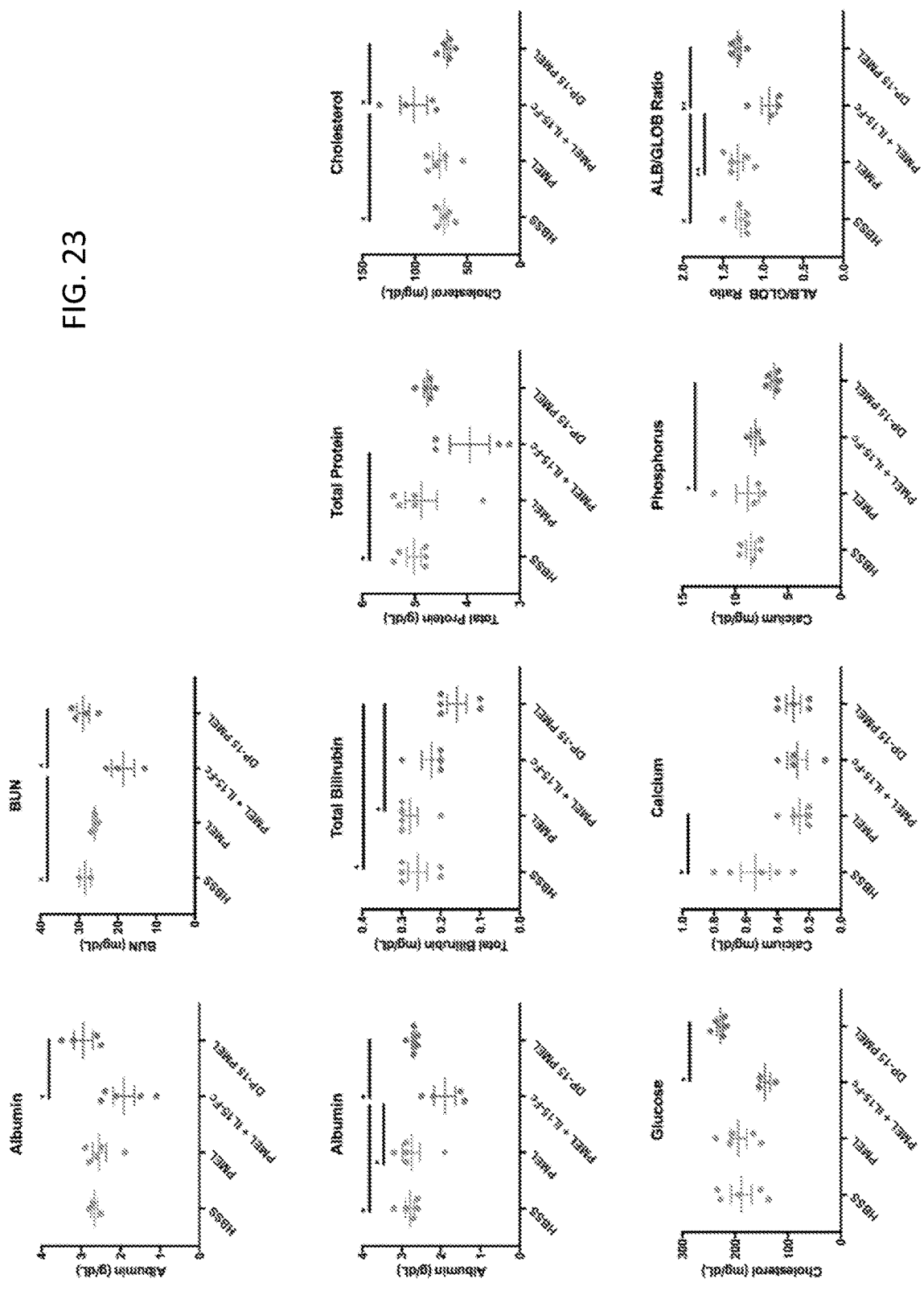
FIG. 23: Clinical chemistry parameters in naive mice at D1 and D4 post-dose. HBSS=vehicle control; DP-15 PMEL=Deep IL-15 Primed PMEL cells; D=Day. Statistical comparisons were made using ANOVA followed by Tukey's multiple comparison test. $*=p<0.05$; $=p<0.01$; $*=p<0.001$; $****=p<0.0001$.

Clinical chemistry parameters were measured on serum samples. FIG. 23 shows clinical chemistry parameters where statistically significant changes were observed for the naïve mice at D1 and D4 post-dose. At D1 post-dose, a significant reduction ($p<0.05$) in Albumin levels was observed in the PMEL+IL15-Fc group relative to the Deep IL-15 Primed PMEL group as well as in the Blood Urea Nitrogen (BUN) levels compared to both vehicle control and Deep IL-15 Primed PMEL ($p<0.05$ for both). At D4 post-dose, the PMEL+IL15-Fc group showed significantly reduced Albumin ($p<0.05$ compared to all the other treatment groups), total protein ($p<0.05$ compared to vehicle control), Glucose ($p<0.05$ compared to the Deep IL-15 Primed PMEL), Albumin/Globulin (ALB/GLOB) ratio ($p<0.05$ compared to vehicle control, and $p<0.01$ compared to PMEL and Deep IL-15 Primed PMEL). Additionally, the PMEL+IL15-Fc group showed a significant increase ($p<0.05$ compared to vehicle control and Deep IL-15 Primed PMEL) in Cholesterol levels. All treatment groups showed a trend toward a reduction in Calcium levels compared to vehicle control, which was statistically significant with the PMEL group ($p<0.05$). The Deep IL-15 Primed PMEL group showed statistically significant changes in Total Bilirubin ($p<0.05$ compared to vehicle control and PMEL) and Phosphorus ($p<0.05$ compared to PMEL).

Figure 24:
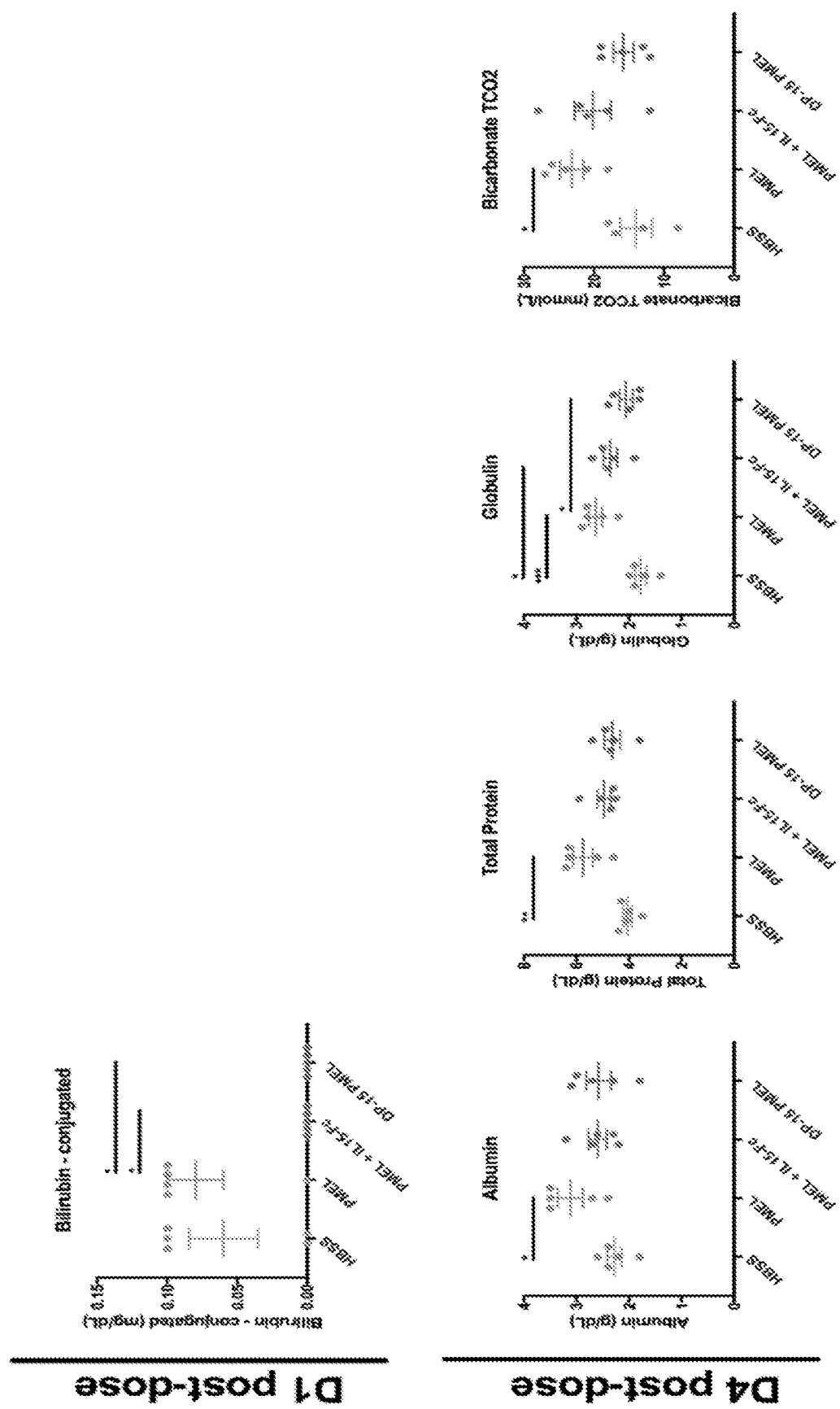
FIG. 24: Clinical chemistry parameters in tumor-bearing mice at D1 and D4 post-dose. HBSS=vehicle control; DP-15 PMEL=Deep IL-15 Primed PMEL cells; D=Day. Statistical comparisons were made using ANOVA followed by Tukey's multiple comparison test. $*=p<0.05$; $=p<0.01$; $*=p<0.001$.

FIG. 24 shows clinical chemistry parameters where statistically significant changes were observed for the tumor-bearing mice at D1 and D4 post-dose. At D1 post-dose, the only statistically significant change in clinical chemistry was a reduction in Bilirubin-conjugated, observed with both the PMEL+IL15-Fc and with the Deep IL-15 Primed PMEL group ($p<0.05$ compared to vehicle control for both). At D4 post-dose, statistically significant increases in Albumin ($p<0.05$ compared to vehicle control), Total Protein ($p<0.01$ compared to vehicle control) and Bicarbonate TCO2 ($p<0.05$ compared to vehicle control) were seen with the PMEL group. Additionally, a statistically significant increase in Globulin was observed with the PMEL group ($p<0.001$ compared to vehicle control; and $p<0.05$ compared to DP-15 PMEL) and with the PMEL+IL15-Fc group (p<0.05 compared to vehicle control).

Systemic Cytokine Release

Figure 25:
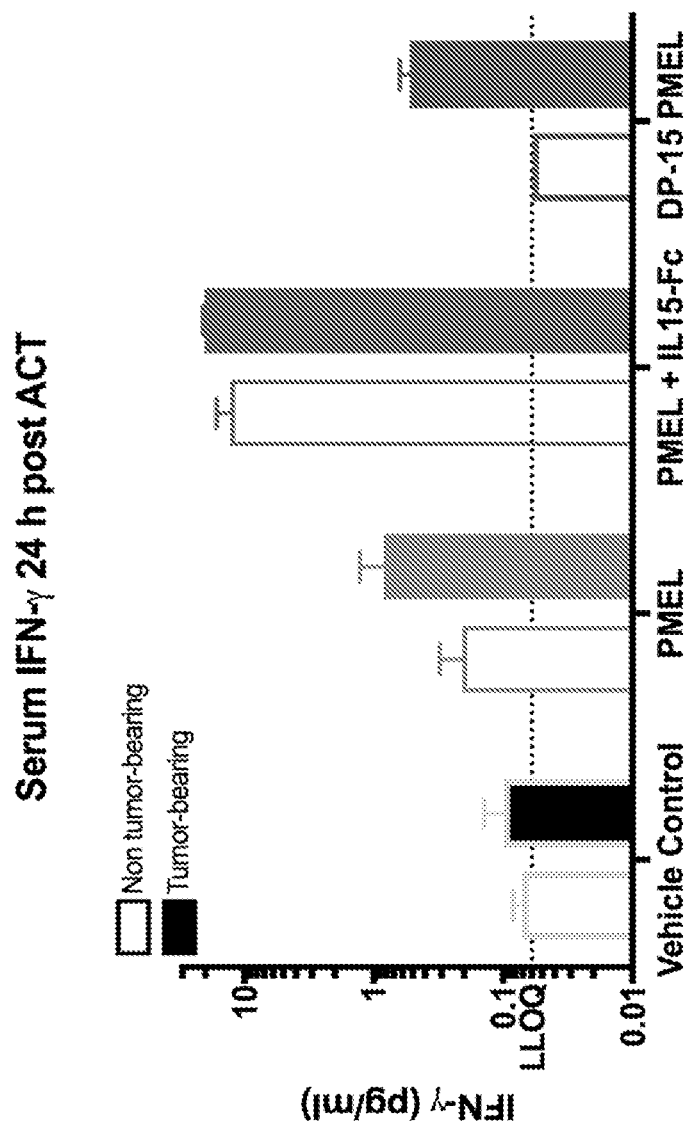
FIG. 25: Serum levels of IFN-γ in tumor-bearing compared to naïve mice 24 hr after ACT. The serum levels of IFN-γ in the PMEL+IL15-Fc group were significantly increased (2-way ANOVA with Tukey's multiple comparison, $p<0.001$) compared to both the PMEL and DP-15 PMEL groups in both naïve and tumor-bearing mice. ACT=adoptive cell transfer; DP-15 PMEL=Deep IL-15 Primed PMEL cells.

Using a Luminex 5-plex kit, serum cytokines (IFN-γ, IL-2, IL-4, IL-6, and TNFα) were measured at 2 hr, 24 hr and 96 hr post-dose. In the naïve non-tumor bearing mice, the levels of IFN-γ in the PMEL+IL15-Fc group were 12.8±3.7 pg/mL, while IFN-γ was below the lower limit of quantitation (LLOQ=0.06 pg/mL) in the Deep IL-15 Primed PMEL group (FIG. 25). In the tumor-bearing mice, there was on average a 41-fold higher IFN-γ concentration in the PMEL+IL15-Fc group (20.5±0.5 pg/mL) compared to the Deep IL-15 Primed PMEL group (0.5±0.1 pg/mL). Higher levels of IL-2, IL-6, and TNFα were also seen in the PMEL+IL15-Fc group compared to the other groups.

Pharmacokinetics of IL15-Fc in the Blood

A sandwich ELISA (anti-Fc capture antibody followed by anti-IL15 detection antibody) was used to measure IL15-Fc in the blood of mice injected with PMEL+IL15-Fc (10 μg) and Deep IL-15 Primed PMEL (carrying 58.5 ug of IL15-Fc).

The pharmacokinetics (PK) of a single dose administration of Deep IL-15 Primed PMEL and PMEL+IL15-Fc were determined for a composite animal in naïve and tumor-bearing mouse. For the PMEL+IL15-Fc group, maximum concentration (Cmax) was attained at 2 hr post dose administration in both naïve and tumor-bearing mice. In the Deep IL-15 Primed PMEL group, the first concentration measured was at 24 hr (the 2 hr samples were initially measured at a non-optimal dilution and no IL15-Fc was detected, and there was not sufficient sample available to repeat the measurement with ideal dilution). Tumor-bearing mice attained slightly lower concentrations than the naïve mice. The calculated mean t½ for IL15-Fc in the PMEL+IL15-Fc group was 28.9 hr and 7.12 hr in tumor bearing mice and non-tumor bearing mice, respectively.

Figure 26:
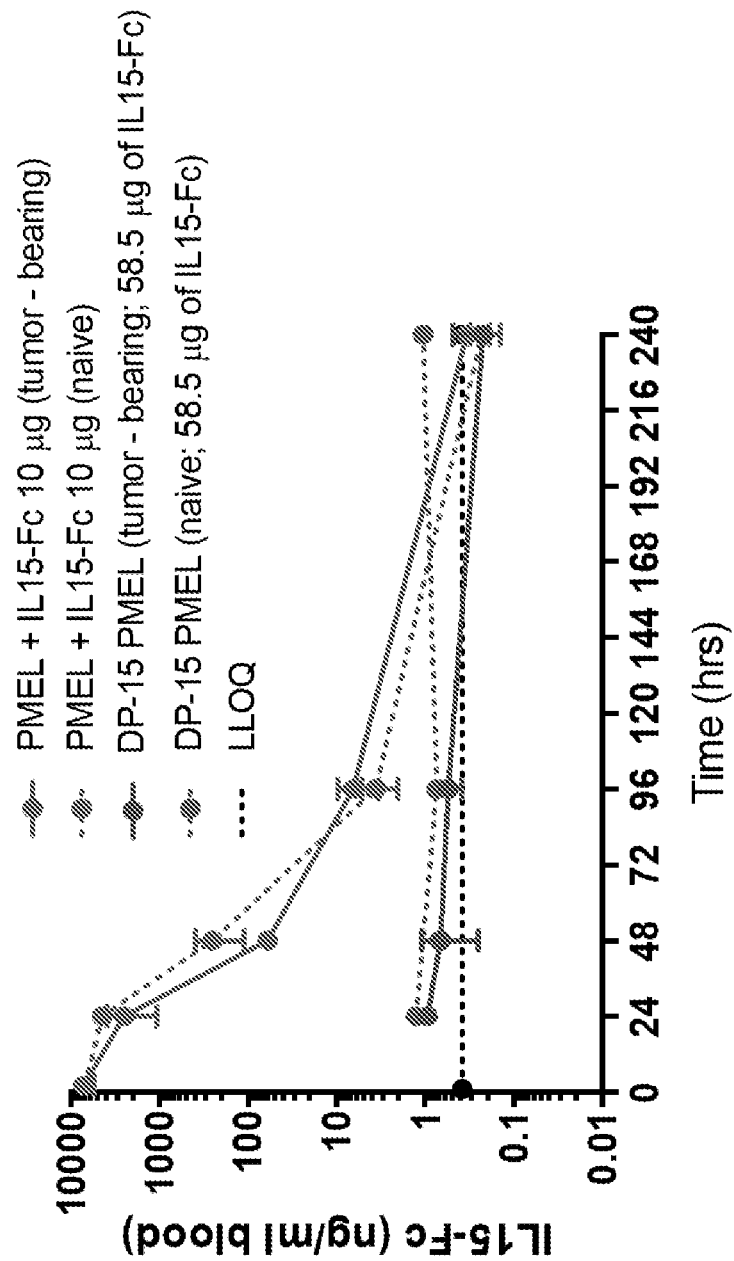
FIG. 26: IL15-Fc systemic exposure in mice treated with PMEL+IL15-Fc and Deep IL-15 Primed PMEL cells, in naïve and tumor-bearing mice.

The IL15-Fc concentrations at the 24 hr timepoint were compared between the PMEL+IL15-Fc and Deep IL-15 Primed PMEL groups. The total IL15-Fc concentration was higher in the PMEL+IL15-Fc (10 μg) group than in the Deep IL-15 Primed PMEL group (58.5 ug of IL15-Fc), approximately 3488-fold higher in the naïve mice and 3299-fold higher in the tumor bearing mice. Composite IL15-Fc PK parameters are summarized in Table 1 and the mean (SD) IL15-Fc PK profiles are depicted in FIG. 26.

Figure 27:
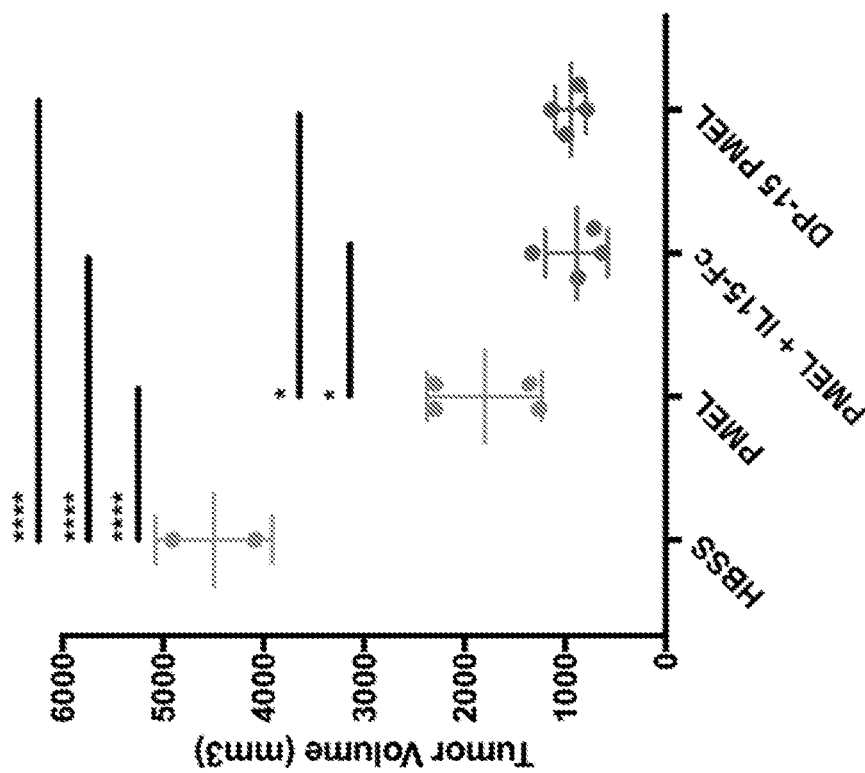
FIG. 27: Mean tumor volume over time and on Day 16. Tumor volumes were measured on D −5, Day −3, D0, D1, D2, D4, D6, D9, D10, D11, D14 and D16. Data are mean±SEM (left panel). Tumor volumes for individual animals on D16 are shown in the right panel. Statistical comparisons were made using ANOVA followed by Tukey's multiple comparison test. $*=p<0.05$; $=p<0.01$; $*=p<0.001$; $****=p<0.0001$. The color of the asterisk represents which groups are statistically different. For example, a green asterisk over the grey (HBSS) line indicates that there is a significant difference between HBSS and PMEL cells. HBSS=vehicle control; ACT=adoptive cell transfer. DP-15 PMEL=Deep IL-15 Primed PMEL cells.
Figure 27:
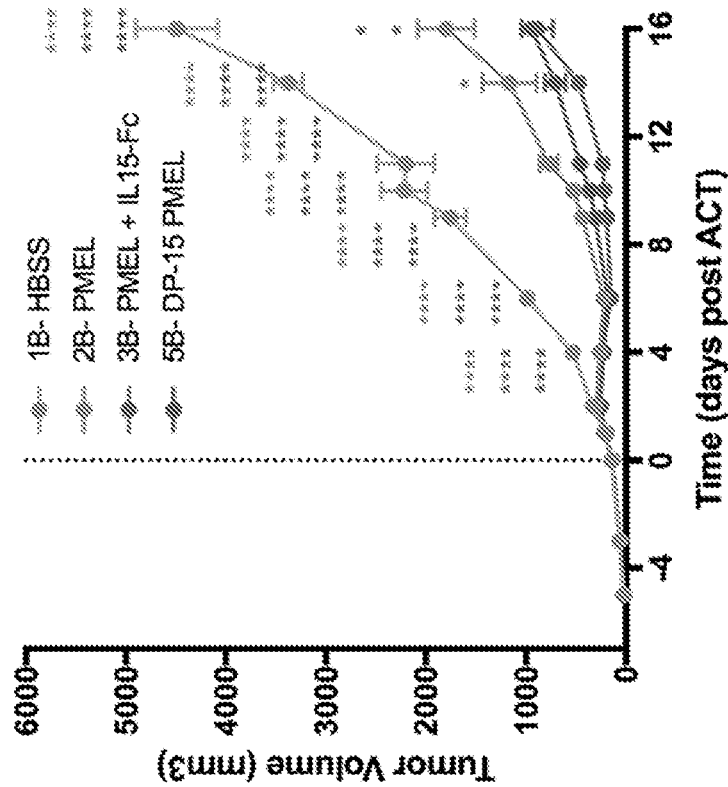
Figure 28:
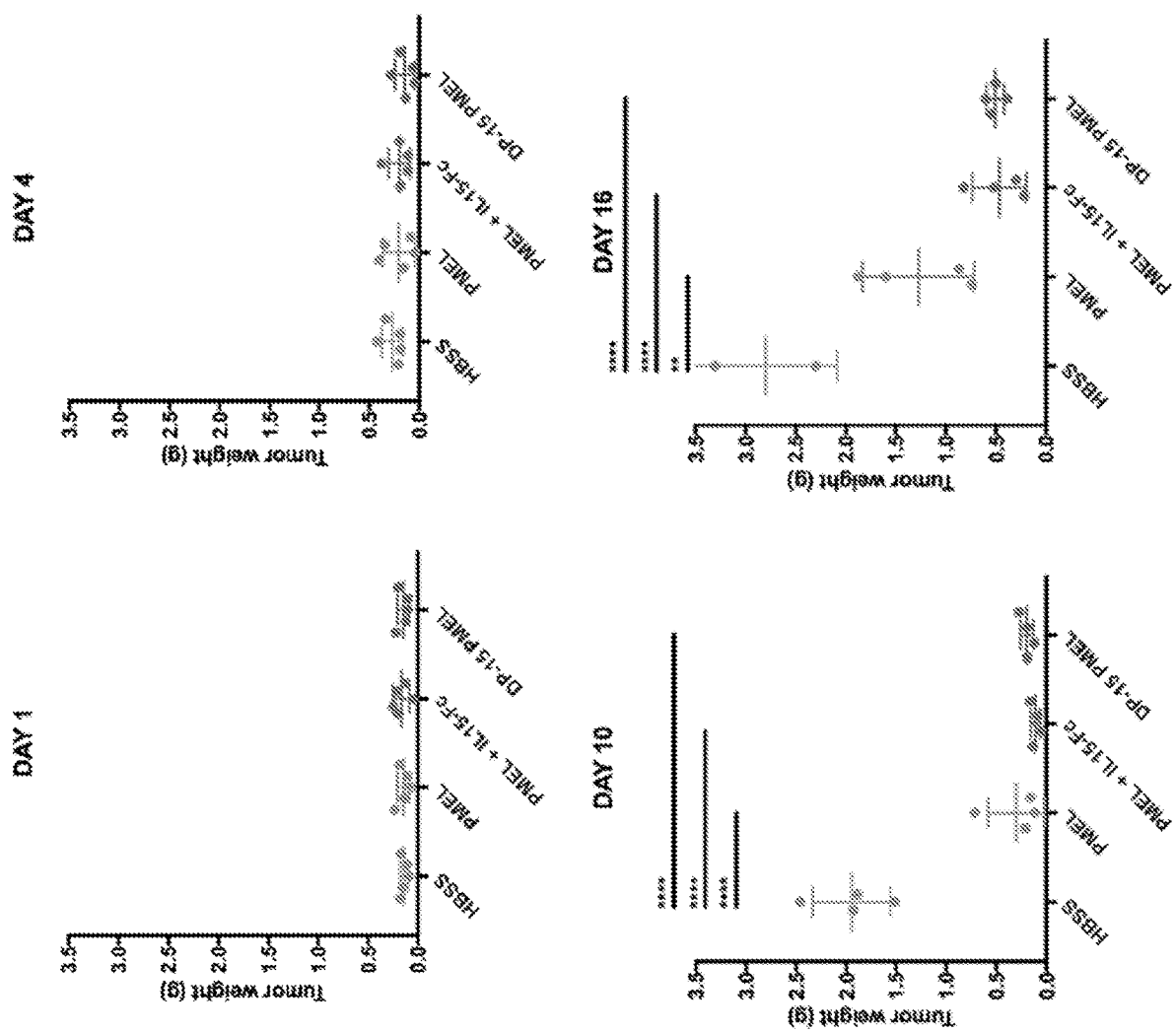
FIG. 28: Mean tumor weight at sacrifice (n=2-5/group/time point). Tumor weights were at sacrifice on Day 1, 4, 10 and 16 (n=2-5/group each time point). Statistical comparisons were made using ANOVA followed by Tukey's multiple comparison test. $*=p<0.05$; $=p<0.01$; $**=p<0.0001$. HBSS=vehicle control; DP-15 PMEL=Deep IL-15 Primed PMEL cells.

(p<0.0001) different from all other groups. Tumor volumes in the PMEL group were significantly (p<0.05) larger than those in the Deep IL-15 Primed PMEL and PMEL+IL15-Fc groups. The inhibition of tumor growth in the PMEL+IL15-Fc and Deep IL-15 Primed PMEL groups were not different from each other on D16 (FIG. 27, left and right panels). Tumors were weighed post-sacrifice (n=2-5, each group, each time point) on D1, 4, 10 and 16 post-dose. Tumor weights are shown in FIG. 28.

Some animals were found moribund or dead prior to the study-specified endpoints. These included mice in the vehicle control (4 total: 1 on D9, 1 on D10 and 2 on D14), in the PMEL group (2 total: 1 on D2, and 1 on D6), in the PMEL+IL15-Fc group (2 total: 1 on D9 and 1 on D11) and in the Deep IL-15 Primed PMEL group (2 total: 1 on D9 and 1 on D16). These were not considered related to treatment since they were distributed across groups with the highest numbers (n=4) in the vehicle control. Finally, there was no difference in animals found moribund or dead associated with the Deep IL-15 Primed PMEL group compared to PMEL.

CONCLUSIONS

Major findings of the study are summarized below.
1. Deep IL-15 Primed PMEL cells were well tolerated at the administered dose of 10×10$^6$ cells.
2. Both PMEL, PMEL+IL15-Fc and Deep IL-15 Primed PMEL cells resulted in tumor growth inhibition compared to vehicle control. Inhibition was higher with PMEL+IL15-Fc and Deep IL-15 Primed PMEL cells compared to PMEL
3. No toxicologically relevant clinical chemistry parameter changes were observed with either PMEL or Deep IL-15 Primed PMEL cells. Some changes were observed with PMEL+IL-15 Fc.
4. No changes in serum IFN-γ, TNF-α or IL-6 were detected with PMEL or Deep IL-15 Primed PMEL cells at any time point. Significant changes in serum IFN-γ and TNF-α were observed with PMEL+IL15-Fc at 24 hr. IL-6 was increased with PMEL+IL15-Fc at 2 hr (Non-tumor-bearing (naïve) mice only) and 24 hr.
5. The serum levels of IL15-Fc in the Deep IL-15 Primed PMEL group were over 3000-fold lower compared to

TABLE 1

Composite IL15-Fc PK parameters for the PMEL + IL15-Fc group, in naïve and tumor-bearing mice (10 ug dose of IL15-Fc)

| Animal | Compound | Group | T1/2 (hr) | Cmax (ng/mL) | Tmax (hr) | Clast (ng/mL) | Tlast (hr) | AUClast (hr * ng/mL) | AUCINF (hr * ng/mL) |
|---|---|---|---|---|---|---|---|---|---|
| Composite | IL15-Fc | Non-tumor bearing | 7.12 | 6931 | 2 | 3.64 | 96 | 202387 | 202424 |
|  |  | Tumor Bearing | 28.9 | 7300 | 2 | 0.448 | 240 | 156335 | 156353 |

Inhibition of Tumor Growth

On D0 (the day of dosing) tumors had reached an average volume of approximately 140 mm$^3$. A statistically significant inhibition of tumor growth was observed at D4 post-dose in all treatment groups compared to vehicle control (p<0.0001), and this difference became more pronounced over time (FIG. 27, left panel). On study D16 there were only ⅔ animals remaining in the vehicle control group (the others were sacrificed due to extensive tumor burden) but ⅘ animals remaining in each of the treatment groups. Tumor volumes in the vehicle control group were significantly the levels detected in the PMEL+IL15-Fc group, corresponding to no weight loss, no significant changes in CBCs and in endogenous immune cells (CD8$^+$, NK1.1$^+$ and CD4$^+$ cells), reduced IFN-γ serum levels and associated pharmacological changes compared to the PMEL+IL15-Fc group.

Modifications and variations of the described methods and compositions of the present disclosure will be apparent to those skilled in the art without departing from the scope and spirit of the disclosure. Although the disclosure has been described in connection with specific embodiments, it should be understood that the disclosure as claimed should not be unduly limited to such specific embodiments. Indeed, various modifications of the described modes for carrying out the disclosure are intended and understood by those skilled in the relevant field in which this disclosure resides to be within the scope of the disclosure as represented by the following claims.

INCORPORATION BY REFERENCE

All patents and publications mentioned in this specification are herein incorporated by reference to the same extent as if each independent patent and publication was specifically and individually indicated to be incorporated by reference.

The invention claimed is:

1. A compound represented by the formula:

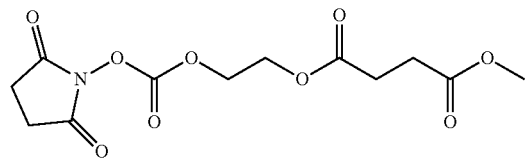

2. A compound represented by the formula:

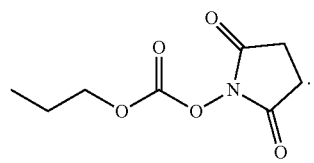

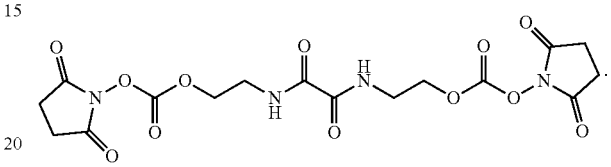

* * * * *